(12) United States Patent
Fujii et al.

(10) Patent No.: US 8,845,966 B2
(45) Date of Patent: Sep. 30, 2014

(54) METHOD FOR MEASURING ANALYSIS OBJECT AND MEASURING DEVICE

(71) Applicant: Panasonic Corporation, Osaka (JP)

(72) Inventors: Takaaki Fujii, Ehime (JP); Yoshifumi Takahara, Ehime (JP); Noriyoshi Terashima, Kanagawa (JP)

(73) Assignee: Panasonic Corporation, Osaka (JP)

( * ) Notice: Subject to any disclaimer, the term of this patent is extended or adjusted under 35 U.S.C. 154(b) by 14 days.

(21) Appl. No.: 13/707,971

(22) Filed: Dec. 7, 2012

(65) Prior Publication Data

US 2013/0140178 A1  Jun. 6, 2013

Related U.S. Application Data

(62) Division of application No. 12/485,193, filed on Jun. 16, 2009, now Pat. No. 8,349,259.

(30) Foreign Application Priority Data

Jun. 16, 2008  (JP) .................................. 2008-157259

(51) Int. Cl.
| | |
|---|---|
| *G01N 15/06* | (2006.01) |
| *G01N 33/00* | (2006.01) |
| *G01N 33/48* | (2006.01) |
| *G01N 33/543* | (2006.01) |
| *G01N 27/327* | (2006.01) |
| *C12Q 1/00* | (2006.01) |

(52) U.S. Cl.
CPC .......... *G01N 27/327* (2013.01); *G01N 33/5438* (2013.01); *G01N 27/3274* (2013.01); *C12Q 1/006* (2013.01)
USPC ...... 422/68.1; 422/50; 422/82.01; 422/82.02; 422/82.12; 436/43; 436/63

(58) Field of Classification Search
USPC ............................. 422/50, 68.1, 82.01, 82.02
See application file for complete search history.

(56) References Cited

U.S. PATENT DOCUMENTS

| | | | |
|---|---|---|---|
| 4,500,031 | A | 2/1985 | Pettingell |
| 4,963,195 | A | 10/1990 | Kodato et al. |
| 5,102,470 | A | 4/1992 | Kodato et al. |
| 6,576,117 | B1 | 6/2003 | Iketaki et al. |
| 6,635,167 | B1 | 10/2003 | Richards et al. |
| 6,780,296 | B1 | 8/2004 | Bhullar et al. |
| 7,510,643 | B2 | 3/2009 | Bhullar et al. |
| 2004/0238357 | A1 | 12/2004 | Bhullar et al. |
| 2005/0019219 | A1 | 1/2005 | Oshiman et al. |

FOREIGN PATENT DOCUMENTS

| | | |
|---|---|---|
| JP | 08-015049 | 1/1996 |
| JP | 10-160592 | 6/1998 |
| JP | 2000-081409 | 3/2000 |
| JP | 2002-372512 | 12/2002 |
| JP | 2003-156469 | 5/2003 |
| JP | 2004-101514 | 4/2004 |
| JP | 3595315 | 9/2004 |
| JP | 2005-265629 | 9/2005 |
| JP | 2006-275713 | 10/2006 |
| WO | 99/60391 | 11/1999 |
| WO | 03/062812 | 7/2003 |

*Primary Examiner* — Brian J Sines
(74) *Attorney, Agent, or Firm* — Wenderoth, Lind & Ponack, L.L.P.

(57) ABSTRACT

The measurement device comprises a sensor holder to which is removable to a biosensor. The sensor holder has measurement-use connection terminals that are in contact with the electrode system in the biosensor and are used to take off signals required for measuring the specific component, and thermocouple-use connection terminals that are in contact with the thermocouple in the biosensor and are used to take off the thermoelectromotive force signals.

19 Claims, 14 Drawing Sheets

METHOD FOR MEASURING ANALYSIS OBJECT AND MEASURING DEVICE

CROSS-REFERENCE TO RELATED APPLICATIONS

This application claims priority to Japanese Patent Application No. 2008-157259. The entire disclosures of Japanese Patent Application No. 2008-157259 are hereby incorporated herein by reference.

BACKGROUND

1. Technical Field

The present invention relates to an analyzer for measuring a highly contaminating/infectious analysis object, and more particularly relates to an analyzer with a disposable sensor, and to a constitution and measurement method for providing high assay accuracy.

2. Description of the Prior Art

In the field of sensors, when the analysis object as a sample is a substance of biological origin, this is specifically referred to as biosensing, and analytical devices used for this are called biosensing devices.

Biosensing devices include those in which the molecular recognition ability of microbes, enzymes, antibodies, and other such biomaterials is utilized among the measurement factors of a sensor that recognizes an analysis object, and a biomaterial is used as a molecular identification element. Specifically, materials of biological origin are used to send out signals proportional to concentration and the like, and so forth. In particular, we have seen the practical application of biosensors that make use of the immune response of antibodies or enzyme reactions, and these biosensors are widely used in the medical field and in the food safety field. Qualitative and quantitative methods that have been developed span a wide range, including electrochemical analysis and optical analysis. Also, when a highly contaminating/infectious analysis object is to be measured with a small sensing device, a disposable sensor is usually used in which the sensor portion that comes into contact with the sample can be removed.

In particular, with analyzers in the medical field related to the health of humans, when disposable sensors are used to prevent secondary infection, because of the important role of such devices, they need to have high measurement accuracy. Accordingly, with biosensing devices in the medical field, various corrections are made to the measured values for the specific components in the analysis object in order to achieve higher measurement accuracy. For instance, there is temperature correction, correction of measurement error due to similar substances, correction of interfering substances, and so forth, and when the analysis object is blood, there is a special hematocrit value correction. In turn, optimization of a calibration line and a sensor by lot management, and the like probably fall under the heading of correction.

Temperature is an especially important factor since it affects all physical and chemical reactions. For example, in the measurement of a specific component in an analysis object, if the ambient measurement temperature is higher than a reference temperature for which a calibration line has been set (although this does not apply unconditionally), there will be acceleration at various analysis (reaction) stages, and the measurement result will probably be greater than the actual true value, and if the temperature is lower than the set reference, the reverse may be true.

One commonly adopted method for solving this problem is to provide an environmental temperature sensor within the measurement device, select the value thereof as the temperature of the reaction region, and subject the specimen concentration value to temperature correction. This method, however, just involves artificially using the environmental temperature as the ambient measurement temperature, so error will occur if there is deviation between the temperature of the measurement component (or more precisely, the measurement region) and the environmental temperature. Particularly with extremely small measurement devices that are held in the hand, a discrepancy from the actual environmental temperature tends to occur when the device is warmed by the body heat of the user at the stage of preparing to measure.

In view of this, there has been a need for a way to measure and correct the temperature of an analysis object measurement component to achieve more accurate temperature correction (see Patent Citations 1 and 2, for example).

For instance, in Patent Citation 1 (Japanese Patent No. 3,595,315), the constitutions shown in FIG. 13a, which is an exploded diagram of a sensor, and FIG. 13b, which illustrates a measurement device in which a sensor has been inserted, are discussed. A thermally conductive layer 824 is provided to part of the sensor, and the temperature of the measurement component is transferred to the end of the sensor inserted in the measurement device. The measurement device is equipped with a temperature sensor 832 that measures the temperature through direct contact with this thermally conductive layer, measures the amount of heat transferred, and subjects the measured specific component concentration information to temperature correction.

In Patent Citation 2 (International Laid-Open Patent Application 2003/062812 pamphlet), the constitution shown in FIG. 14, which is a cross section of the main components of a measurement device in which a sensor is inserted, is discussed. A thermally conductive layer 912B is provided to a sensor holder directly under the analysis object measurement component of the sensor, the measurement device is further equipped with a temperature sensor 912A that comes into direct contact with this layer, the transferred heat or the direct temperature of the sensor is measured, and the measured specific component concentration information is subjected to temperature correction.

SUMMARY

Nevertheless, with the constitution discussed in Patent Citation 1 or 2, the temperature of the analysis object or the measurement component is measured indirectly, and direct measurement is impossible. Another problem with the constitution discussed in Patent Citation 1 is that if the thermally conductive layer between the measurement component and the temperature sensing unit comes into contact with a fingertip or other such thermal element that is different in temperature from that of the analysis object, the accuracy of the measured temperature suffers. Moreover, since the temperature of the measurement device is, of course, also readily transferred to the thermally conductive layer, it would seem to be extremely difficult to accurately measure the temperature of the measurement region. Also, with the constitution discussed in Patent Citation 2, a temperature sensing unit is provided directly under the measurement component. With this constitution, however, a sensor substrate is sandwiched in between, and the thermal conductivity of the plastic resins used for sensor substrates is generally extremely low. Consequently, even though a thermally conductive layer is installed on the measurement device side, specific changes in the temperature of the measurement region cannot be ascertained. Furthermore, it remains uncertain whether accurate measurement is possible in a situation in which there is a substrate (an adiabatic material). Also, just as in Patent Citation 1, the effect of heat transferal to the measurement device side probably cannot be eliminated.

It is an object of the present invention to solve the above-mentioned problems encountered in the past, and to provide an analysis object measurement method, and a measurement device with which the effect of temperature due to measurement conditions can be kept to an absolute minimum, and a specific component of an analysis object can be measured accurately.

The analysis object measurement method pertaining to the present invention is a method for measuring an analysis object in which a specific component in an analysis object is measured with a biosensor system comprising a holder for holding the analysis object, an electrode system for measuring the analysis object, and a thermocouple formed by joining at least two dissimilar substances, said method comprising a specimen measurement step, a temperature information computation step, and a temperature compensation step. In the specimen measurement step, a specific component is measured in a spot of the analysis object that has been applied to the holder. In the temperature information computation step, temperature information is acquired using the thermocouple. In the temperature compensation step, the value measured in the specimen measurement step is corrected on the basis of the temperature information.

The measurement device pertaining to the present invention comprises a sensor holder to which is removable to a biosensor. The sensor holder has measurement-use connection terminals that are in contact with the electrode system in the biosensor and are used to take off signals required for measuring the specific component, and thermocouple-use connection terminals that are in contact with the thermocouple in the biosensor and are used to take off the thermoelectromotive force signals.

Also, an analyzer that realizes the present invention has a constitution comprising a thermocouple or an compensating lead wire thereof that is connected to a thermocouple-use connection terminal within the measurement device, and having a reference temperature/environmental temperature sensor that measures the temperature of the reference temperature junction that is the end thereof, or has a constitution in which a thermocouple ends on a biosensor, having a reference temperature junction temperature sensor that measures the temperature of the reference temperature junction that is the end thereof in the sensor holder.

DETAILED DESCRIPTION

Embodiments of the temperature-compensating analyzer (biosensor system) and method thereof (method for measuring an analysis object) of the present invention will now be described in detail along with the drawings.

Embodiment 1

The temperature-compensating analyzer and method thereof of Embodiment 1 will now be described on the basis of FIGS. 1 to 9.

The case described here is a blood glucose sensor, in which blood is used as the analysis object and the glucose concentration (measured value) is measured as the specific component. Naturally, FIGS. 1 to 9 are merely embodiments of the present invention, and the invention is not limited to or by these drawings.

Figure 1:
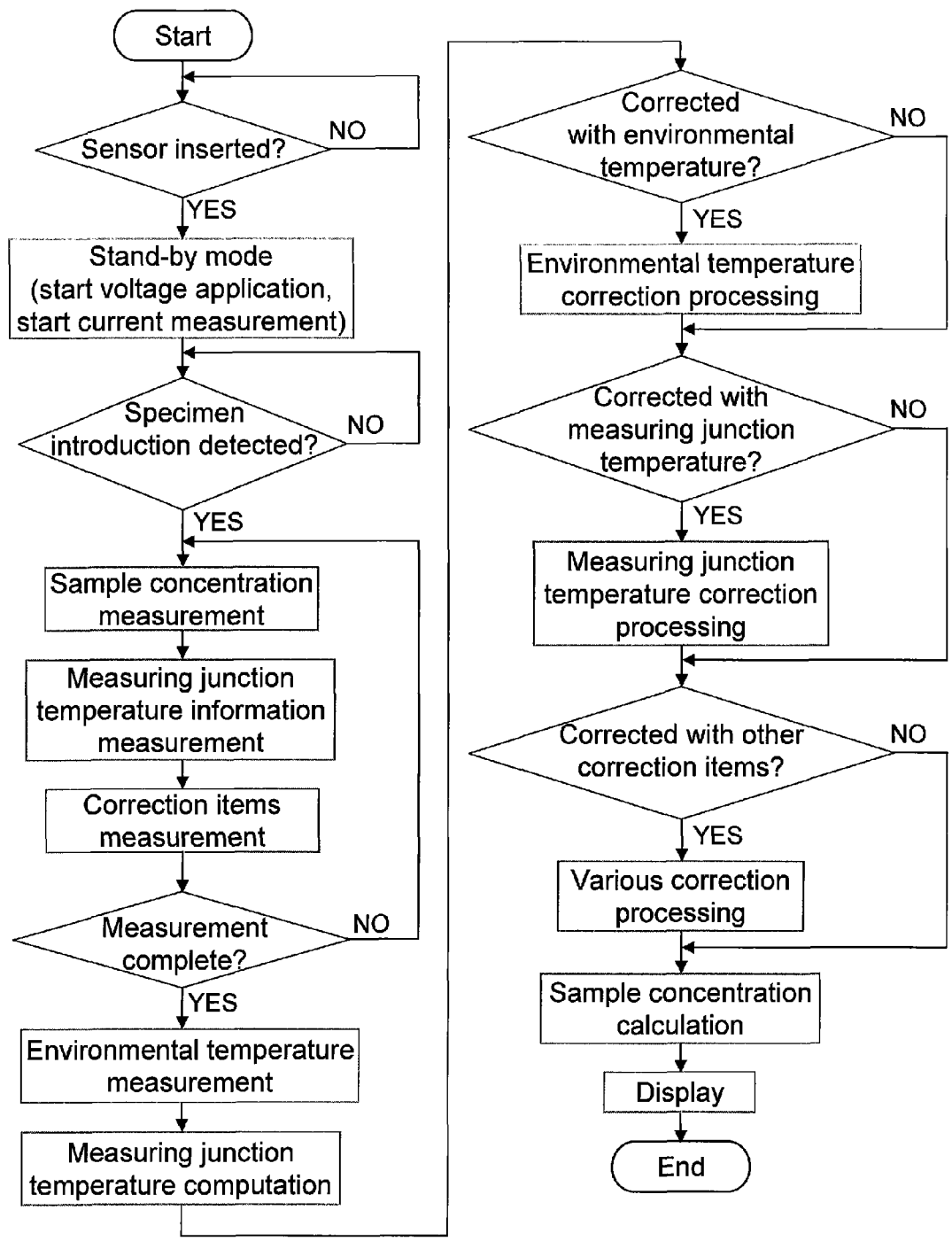
FIG. 1 is a simplified flowchart of the temperature-compensating analyzer pertaining to an embodiment of the present invention, and of the measurement algorithm in the method thereof.
Figure 2:
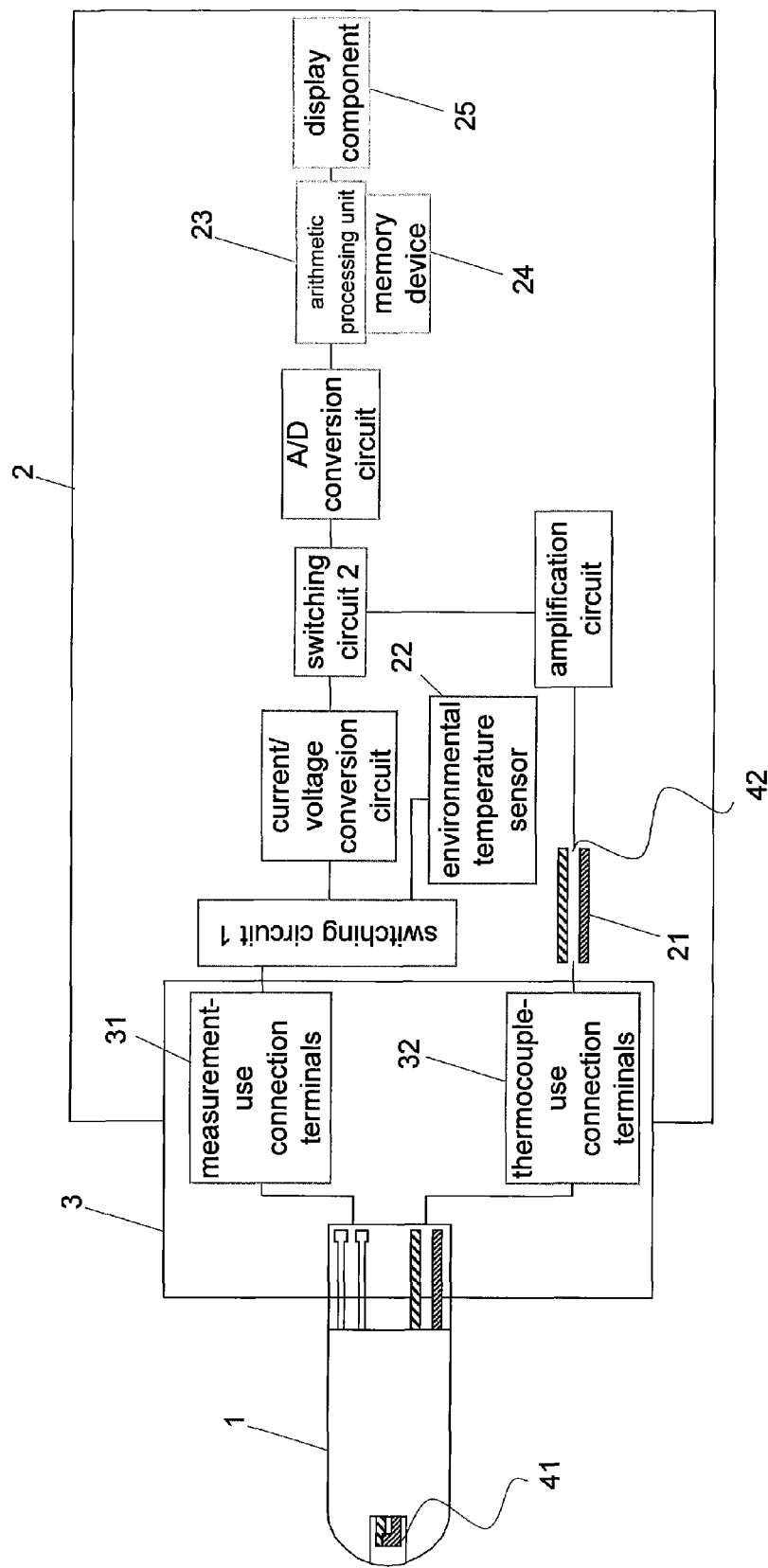
FIG. 2 is a simplified diagram of the configuration of the analyzer in FIG. 1.

FIG. 1 is a diagram of the overall algorithm when a blood glucose value sensor (biosensor) 1 is mounted in a measurement device 2, and a specific component concentration is then measured. FIG. 2 is a simplified diagram of the overall configuration of an analyzer (biosensor system) when the blood glucose value sensor 1 is mounted to the measurement device 2.

Next, the blood glucose value sensor 1, which is a constituent element of the analyzer and method of this embodiment, will be described in detail.

Figure 3:
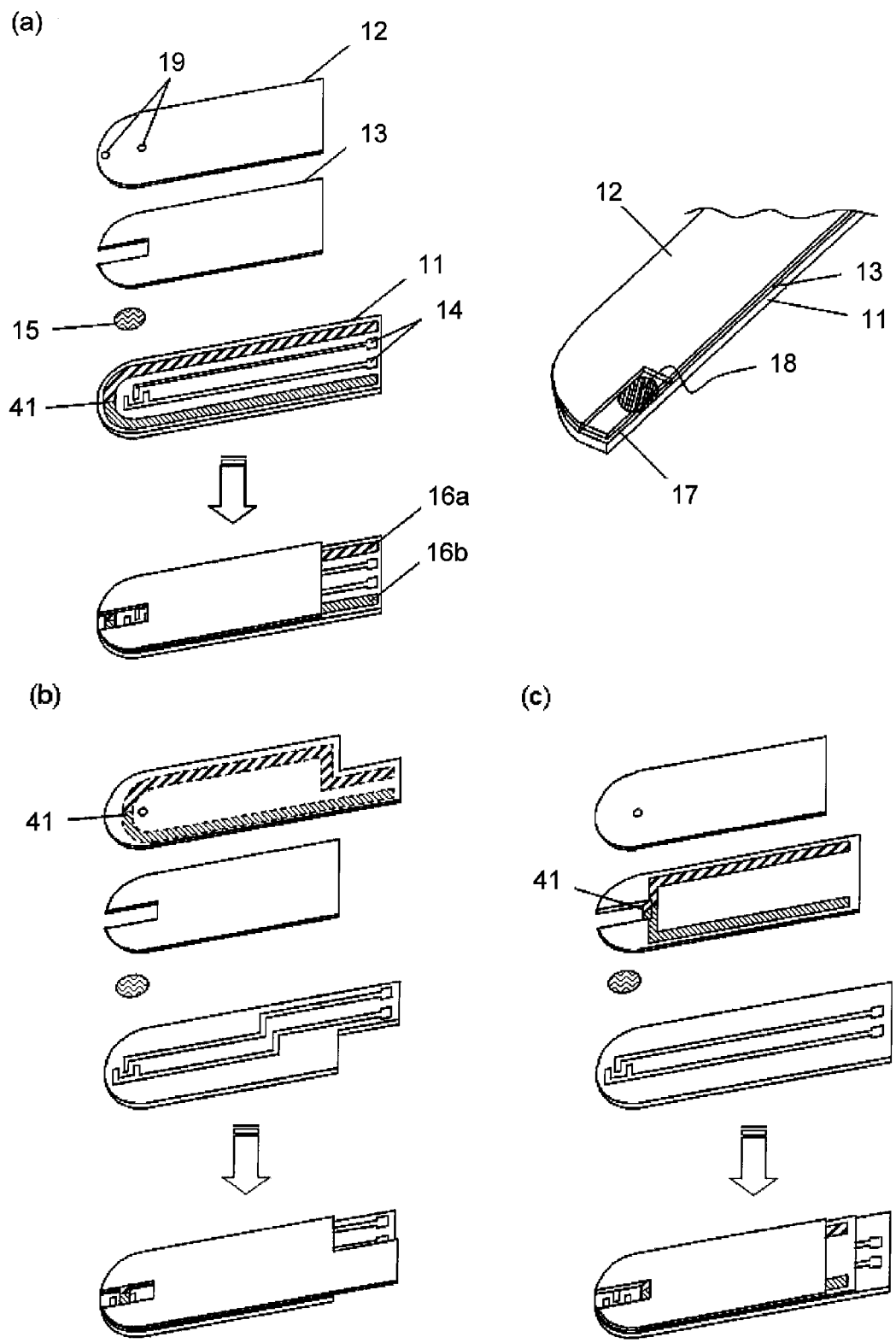
FIGS. 3a, 3b, and 3c are simplified diagrams of the configuration of the sensor component in the temperature-compensating analyzer of the present invention.

FIG. 3 is a representative exploded perspective view of the blood glucose value sensor 1.

In this embodiment, the blood glucose value sensor 1 can be manufactured by laminating a substrate (first substrate) 11, a spacer (third substrate) 13, and a cover (second substrate) 12 in that order and integrating them.

There are no particular restrictions on the material of the substrate 11 other than that it be insulating, but examples include polyethylene terephthalate (PET), polyethylene naphthalate (PEN), polycarbonate (PC), polyimide (PI), polyethylene (PE), polypropylene (PP), polystyrene (PS), polyvinyl chloride (PVC), polyoxymethylene (POM), monomer cast nylon (MC), polybutylene terephthalate (PBT), methacrylic resin (PMMA), ABS resin (ABS), glass, and silicon substrates. Of these, polyethylene terephthalate (PET), polyethylene naphthalate (PEN), polycarbonate (PC), and polyimide (PI) are preferable, and polyethylene terephthalate (PET) is particularly favorable. There are no particular restrictions on the size of the substrate 11, but when it is in the form of a board as depicted, for example, it may have an overall length of 5 to 100 mm, a width of 3 to 50 mm, and a thickness of 0.05 to 2 mm, and preferably will have an overall length of 10 to 70 mm, a width of 3 to 30 mm, and a thickness of 0.1 to 1 mm, and more preferably will have an overall length of 10 to 40 mm, a width of 5 to 10 mm, and a thickness of 0.1 to 0.6 mm.

In this embodiment, there are no particular restrictions on the material of the spacer 13 other than that it be insulating, but the same materials as those listed for the substrate 11 can be used, for example. There are no particular restrictions on the size of the spacer 13, but when it is in the form depicted, for example, it may have an overall length of 5 to 100 mm, a width of 3 to 50 mm, and a thickness of 0.01 to 1 mm, and preferably will have an overall length of 10 to 70 mm, a width of 3 to 40 mm, and a thickness of 0.05 to 0.5 mm, and more preferably will have an overall length of 10 to 30 mm, a width of 5 to 10 mm, and a thickness of 0.05 to 0.25 mm. A notch is formed in the spacer 13, which when flanked by the substrate 11 and the cover 12 serves as a channel for introducing an analysis object as a sample, and forms a cavity (holder) 17 for holding the analysis object. The size thereof is determined by the volume of the sample to be measured and by the thickness. The notch may be formed, for example, by cutting or piercing with a laser, a die, or the like. Also, one of the substrates may be produced in three-dimensional mold so as to form the cavity 17. In this case, a sensor may be formed by two substrates.

There are no particular restrictions on the material of the cover 12 in this embodiment, and the same materials as those listed for the substrate 11 can be used, for example, but the material is preferably transparent or semi-transparent so that the introduced sample will be easy to see. Also, if an electrode is provided over the cover 12 as discussed below, the material must be insulating. Preferably, the portion of the cover 12 corresponding to the roof of the cavity 17 is subjected to a hydrophilic treatment. Examples of hydrophilic treatments include a coating with a surfactant, and introducing hydrophilic functional groups such as hydroxyl groups, carbonyl groups, or carboxyl groups, to the cover surface by plasma treatment or the like. There are no particular restrictions on the size of the cover 12, but if it has the shape depicted in the drawings, for example, it may have an overall length of 5 to 100 mm, a width of 3 to 50 mm, and a thickness of 0.01 to 0.5 mm, and preferably will have an overall length of 10 to 70 mm, a width of 3 to 30 mm, and a thickness of 0.05 to 0.3 mm, and more preferably will have an overall length of 10 to 40 mm, a width of 5 to 10 mm, and a thickness of 0.05 to 0.2 mm. A hole 19 is preferably formed in the portion of the cover 12 corresponding to the roof of the cavity 17. If the hole 19 is disposed at the distal end of the cavity 17, for example, it may be a sample introduction hole for aiding the introduction of sample, and if disposed on the inner side of the cavity 17, it may be an air vent hole for taking the sample spot smoothly into the cavity 17; thus the role played by the hole varies with where it is disposed. Accordingly, its shape is not limited to being circular, and may instead be elliptical, polyhedral, etc., and a plurality of holes may also be provided. If there is a plurality of holes, the size and shape of each may be varied according to the intended role. The hole 19 may be formed by cutting or piercing with a laser, a die, a drill, etc. Also, in the molding of the cover 12, the mold may be machined so as to allow the hole 19 to be formed.

Next, the integration method for laminating the substrate 11, the spacer 13, and the cover 12 in that order may involve sticking the three members together with an adhesive agent, or may involve thermal fusion bonding. Examples of adhesives that can be used include epoxy adhesives, acrylic adhesives, polyurethane adhesives, thermosetting adhesives (hot melt adhesives, etc.), UV curing adhesives, and so forth.

Next, the configuration of the blood glucose value sensor 1 in this embodiment will be described. A measurement component 18 constituted by a measurement-use reagent 15 and an electrode system 14 for measuring the glucose concentration in a sample is installed in the blood glucose value sensor 1, part of a thermocouple 16 that is a temperature measurement circuit for obtaining temperature information about the measurement component 18 is also installed, and a measuring junction 41 at which are joined the wiring 16a and 16b made of the two different materials of the thermocouples is installed near the measurement component 18.

The two different materials of the thermocouples 16a and 16b are composed of a combination of metal, alloy, and semiconductor, and depending on this combination, the measurement temperature range, the resistance to acidity and alkalinity, and the thermoelectromotive force characteristics will exhibit various features. The manufacturing steps and cost can be reduced by having one of the materials used for the thermocouples 16a and 16b be the same as the material of the electrode system 14.

The electrode system 14 consists of at least a working electrode and a counter electrode, and a reference electrode (not shown) may be provided as well. As for the types thereof, in addition to a measurement electrode, it is often the case that a detection electrode (not shown) for detecting the introduction of a sample, or an electrode for measuring various correction items is installed.

In the case of a blood glucose sensor, the measurement-use reagent 15 includes glucose dehydrogenase or another such redox enzyme, and includes as optional components a mediator, an enzyme stabilizer, a reagent crystal homogenizer, an enzyme reaction stabilizer, or the like. This is usually disposed spanning the working electrode and the counter electrode so as to facilitate electrochemical action between the two electrodes.

Upon being dissolved by the introduction of a sample, the measurement-use reagent 15 undergoes a redox reaction with a specific component contained in the analysis object. At this point, a specific voltage is applied between the working electrode and the counter electrode, which causes current proportional to the concentration of the specific component to flow between the working electrode and the counter electrode.

The voltage applied for measuring specimen concentration is, for example, at least the voltage at which an electron transfer substance including an enzyme or mediator contained in the measurement-use reagent 15 will act with an electrode. This applied voltage is preferably 0.001 to 2.0 V, and more preferably 0.05 to 1.0 V, and even more preferably 0.1 to 0.6 V, when the specimen concentration measurement electrode is a two-electrode type. If the specimen concentration measurement electrode is a three-electrode type, the voltage is applied between the working electrode and the reference electrode, and the applied voltage is −0.5 to 1.5 V, and more preferably −0.2 to 0.6 V, when the reference electrode is made of silver-silver chloride. Meanwhile, the application time is, for example, 0.001 to 60 seconds, and more preferably 0.01 to 10 seconds, and even more preferably 0.01 to 5 seconds.

The wiring between the electrode system 14 and the thermocouple 16 may, for example, be installed on the same substrate 11, as shown in FIG. 3a, or, as shown in FIG. 3b, the wiring for the electrode system 14 may be provided on the substrate 11 side, the wiring for the thermocouple 16 provided on the cover 12 side, so that the wiring is installed on opposing faces of the substrate 11 and the cover 12 flanking the measurement component 18. Furthermore, as shown in FIG. 3c, the constitution may be such that the wiring for the electrode system 14 is provided on the substrate 11 side, the wiring for the thermocouple 16 is provided on the spacer 13, and the measuring junction 41 is located on the side face of the cavity 17. That is, the wiring for the thermocouple 16 and the wiring for the electrode system 14 need not be provided on just the substrate 11, and can be disposed on the cover 12 or the spacer 13 as desired. Whatever the disposition, the measurement component 18, which is made up of the electrode system 14 and the measurement-use reagent 15, and the measuring junction 41, which is the junction of the thermocouples 16a and 16b constituted by joining wiring of two dissimilar materials, are both installed in the cavity 17 so as to come into direct contact with the analysis object that is introduced.

With the blood glucose value sensor 1, one method for installing the wiring for the electrode system 14 and the thermocouple 16 is to form a thin film of the substance constituting the wiring over the entire surface of the constituent member of the blood glucose value sensor 1 by sputtering, vapor deposition, or printing, using a metal, alloy, semiconductor, or the like as the material, and making slits in this thin film with a laser, thereby creating a specific wiring pattern. However, as shown in FIG. 3a, when the electrode system 14 and the thermocouple 16 are provided on the same substrate, it is necessary to form a thin film by mutually masking or otherwise treatment the portions where the electrode system 14 and the thermocouple 16 are formed from different materials. In this case, the junction of the thermocouples 16a and 16b is preferably disposed on the distal end side of the cavity 17, upstream from the electrode system 14. The advantage to this is that there is no need to worry about intersection with the detection electrode (not shown) that is part of the electrode system 14, which means that the manufacturing process can be simplified.

The laser can be, for example, a YAG laser, a CO2 laser, a green laser, an excimer laser, etc. As an alternative method, the wiring may be formed in a restricted area in just a predetermined pattern by screen printing. Or, in sputtering or vapor deposition, masking may be performed just as with screen printing, and then a thin film electrode and thermocouples may be formed in just a predetermined pattern. The wiring pattern is not limited to just what is disclosed in the working examples and so forth, and there are no restrictions as long as the effect of the present invention can be obtained.

The measurement device 2, which is a constituent element of this embodiment, will now be described.

Figure 4:
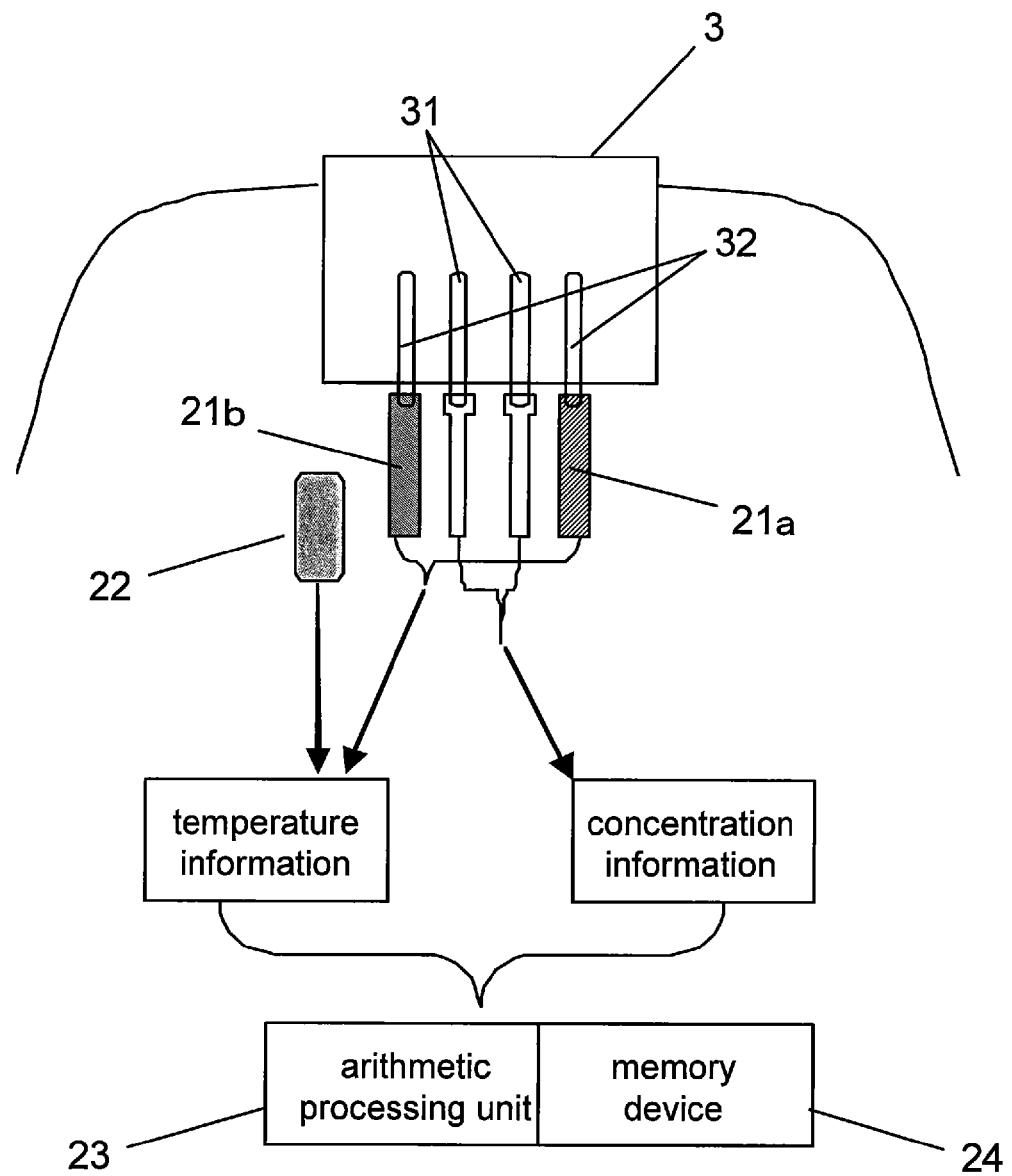
FIG. 4 is a simplified diagram of the configuration of a measurement device in Embodiment 1 of the present invention.

FIG. 4 is a detail enlargement of the portion where the blood glucose value sensor 1 is mounted to the measurement device 2. FIG. 5a is an oblique view of the state before and after the mounting of the blood glucose value sensor 1 to a sensor holder 3 that removably holds the sensor.

Figure 5:
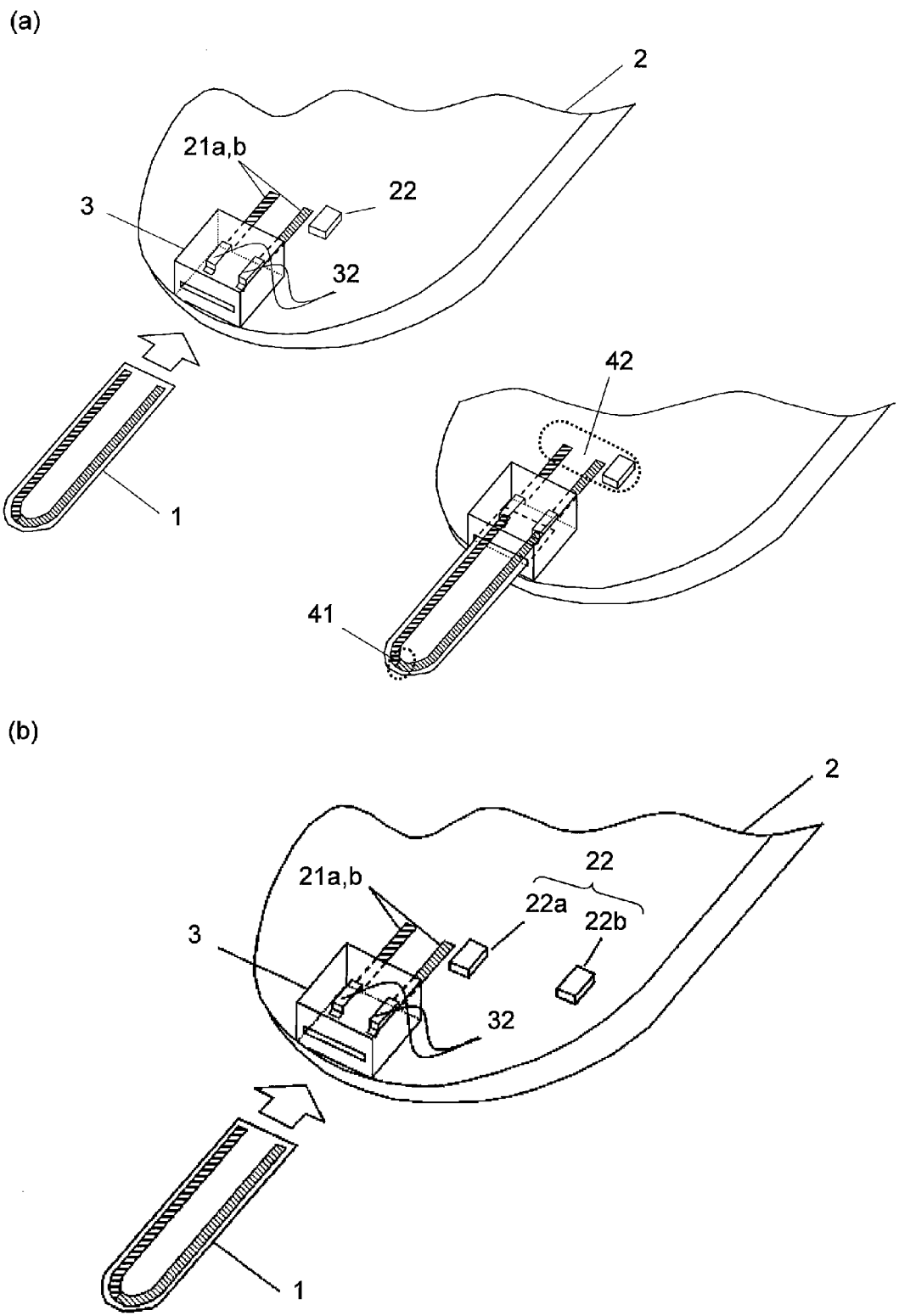
FIGS. 5a and 5b are a simplified diagram of a temperature measurement system in Embodiment 1 of the present invention, a view of the state when the sensor is inserted, and a modification example of an environmental temperature sensor.

As shown in FIGS. 2, 4, and 5, the measurement device 2 constituting this embodiment comprises the sensor holder 3 that removably holds the blood glucose value sensor 1, which is a constituent element just as in this embodiment, and on the inside thereof are installed measurement-use connection terminals 31 and thermocouple-use connection terminals 32, which are respectively corresponding connection terminals for forming electrochemical junctions with the electrode system 14 and the thermocouples 16a and 16b in the blood glucose value sensor. In other words, the ends of both the electrode system 14 and the thermocouples 16a and 16b on the blood glucose value sensor 1 are disposed at locations that come into contact with the connection terminals 31 and 32.

With the measurement-use connection terminals 31, for example, voltage is applied, via a switching circuit, between a detection electrode for detecting the introduction of an analysis object into the cavity 17, or an electrode for measuring the concentration of an analysis object, and an electrode for measuring various correction items. Various kinds of information obtained as current values by measurement with the electrode system 14 and the thermocouples 16a and 16b is converted into voltage via a current/voltage circuit, then converted into a digital signal and sent to an arithmetic processing unit 23. The various correction items referred to here are, for example, hematocrit value correction, correction of interfering substances, etc. Naturally, these are just examples, and all correction items that allow for electrochemical measurement are encompassed, and if some metering function besides electrochemical measurement is added to the measurement device 2 side, then that information is also encompassed.

The thermocouple-use connection terminals 32 are connected to second wires (second thermocouples) 21a and 21b provided ahead of time to the measurement device 2. The second wires 21a and 21b are made of the same material as the thermocouples 16a and 16b on the blood glucose value sensor 1, or are compensating lead wires corresponding to the respective thermocouples. Since a characteristic of a thermocouple is that the temperature difference at a junction where two dissimilar materials are joined is outputted as a thermoelectromotive force, it is possible to compute the temperature difference between junctions, but the temperature of the measuring junction 41 is not known. Accordingly, another junction (the ends of the second wires 21a and 21b in this embodiment (see FIG. 5)) becomes a reference temperature junction 42, and the temperature difference can be measured as a voltage by connecting a voltage gauge directly to these ends. The ends of the second wires 21a and 21b, as discussed above, are the reference temperature junction 42 in a biosensor/measurement device integrated type of thermocouple that is integrated with a sensor. Thus, the two need to be disposed as close as possible, so that there will be no temperature difference between the ends. The distance between the ends is preferably no more than 10 mm, and more preferably no more than 5 mm, and even more preferably no more than 3 mm.

The role of the thermocouple-use connection terminals 32 is to connect the thermocouples 16a and 16b on the blood glucose value sensor 1, or the second wires 21a and 21b in the measurement device 2, and are each made of the same material as the respective thermocouples, or are constituted by compensating lead wires corresponding to the respective thermocouples. The surface of the thermocouple-use connection terminals 32 may also be plated to make them more durable when plugged in and out of the blood glucose value sensor 1, as terminals that also have the function of holding the blood glucose value sensor 1. Alternatively, if the design makes use of a structure or material that will produce as little temperature difference as possible between the ends and the distal ends of the connection terminals, there will be no problem at all with using a material that is different from that of the thermocouples, because of the thermocouple characteristics. For instance, if a material with extremely high thermal conductivity is used, then the temperature at the ends and the distal ends of short connection terminals will be substantially uniform.

As discussed above, a characteristic of a thermocouple is that the temperature difference at a junction where two dissimilar materials are joined is outputted as a thermoelectromotive force, it is possible to compute the temperature difference between junctions, but the temperature of the measuring junction 41 is not known. Accordingly, it is necessary to measure the temperature of the reference temperature junction 42 and measure a reference temperature. Thus, with the measurement device 2 that is a constituent element in this embodiment, an environmental temperature sensor 22 that measures the environmental temperature is installed at the ends of the second wires 21a and 21b, that is, at the reference temperature junction 42, or nearby, and with this structure the temperature is the same at said ends and the environmental temperature sensor 22. Nevertheless, the environmental temperature sensor 22 has two purposes: the function of measuring the environmental temperature, and the function of measuring the reference temperature of the thermocouples. Examples of the environmental temperature sensor 22 include a thermistor, a temperature measuring resistor, an IC temperature sensor, and a radiation thermometer.

Also, as shown in FIG. 5b, for example, the environmental temperature sensor 22 may comprise a first temperature sensor 22a for acquiring the reference temperature of the thermocouples, and a second temperature sensor 22b for acquiring the environmental temperature of the measurement device 2, with these two being provided separately.

Using the blood glucose value sensor 1 and the measurement device 2 is what affords the effect of the present invention. Specifically, when the thermocouples 16a and 16b are installed in the blood glucose value sensor 1 and the second wires (may be compensating lead wires on the measurement device side, as mentioned above) 21a and 21b are installed in the measurement device 2, and when, as shown in FIG. 5, the blood glucose value sensor 1 is mounted to the sensor holder 3 that removably holds the blood glucose value sensor 1, the thermocouples 16a and 16b and the second wires 21a and 21b are linked via the thermocouple-use connection terminals 32 in the sensor holder 3, forming a biosensor/measurement device integrated type of thermocouple. In the blood glucose value sensor 1, the measuring junction 41, which is the distal ends of the thermocouples 16a and 16b, is disposed in the cavity 17 where level of the analysis object is measured, and in the measurement device 2, a pair of thermocouples is formed in which the ends of the second wires 21a and 21b serve as the reference temperature junction 42, and the environmental temperature sensor 22 disposed near the reference temperature junction 42 measures the reference temperature. Consequently, the result is a thermocouple analyzer in which the blood glucose value sensor 1 and the measurement device 2 are integrated. Thus, a thermoelectromotive force is generated if there is a temperature difference between the measuring junction 41 of the thermocouples 16a and 16b, which are in the form of an integrated thermocouple via the thermocouple-use connection terminals 32, and the reference temperature junction 42, which is the ends of the second wires 21a and 21b. This thermoelectromotive force is amplified by an amplifying circuit provided as needed, that information is converted into a digital signal by an A/D converting circuit via a switching circuit, and information about a temperature difference between the measuring junction 41 and the reference temperature junction 42 is transmitted to the arithmetic processing unit 23.

Figure 6:
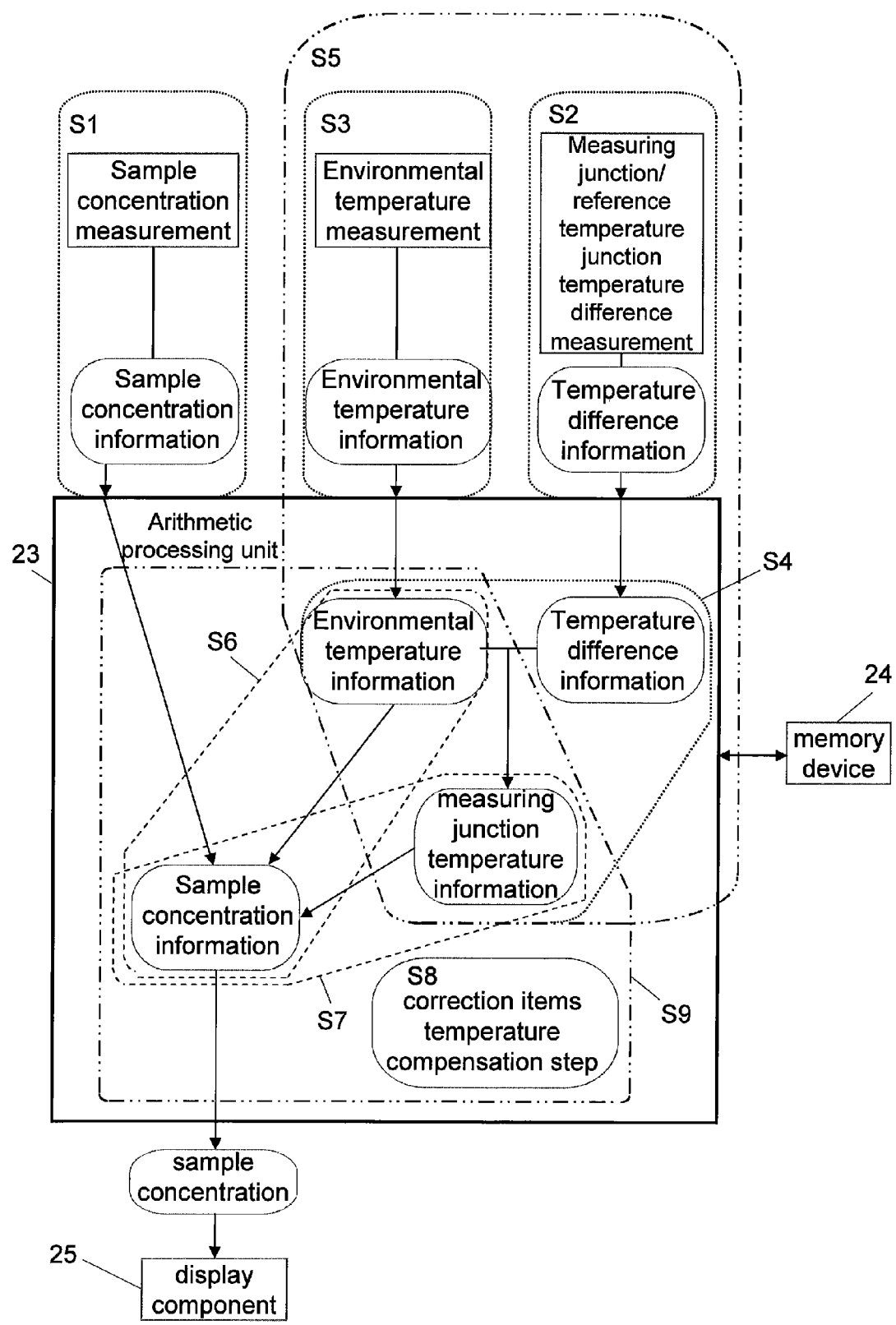
FIG. 6 is a simplified diagram of the measurement system steps in Embodiment 1 of the present invention.
Figure 7:
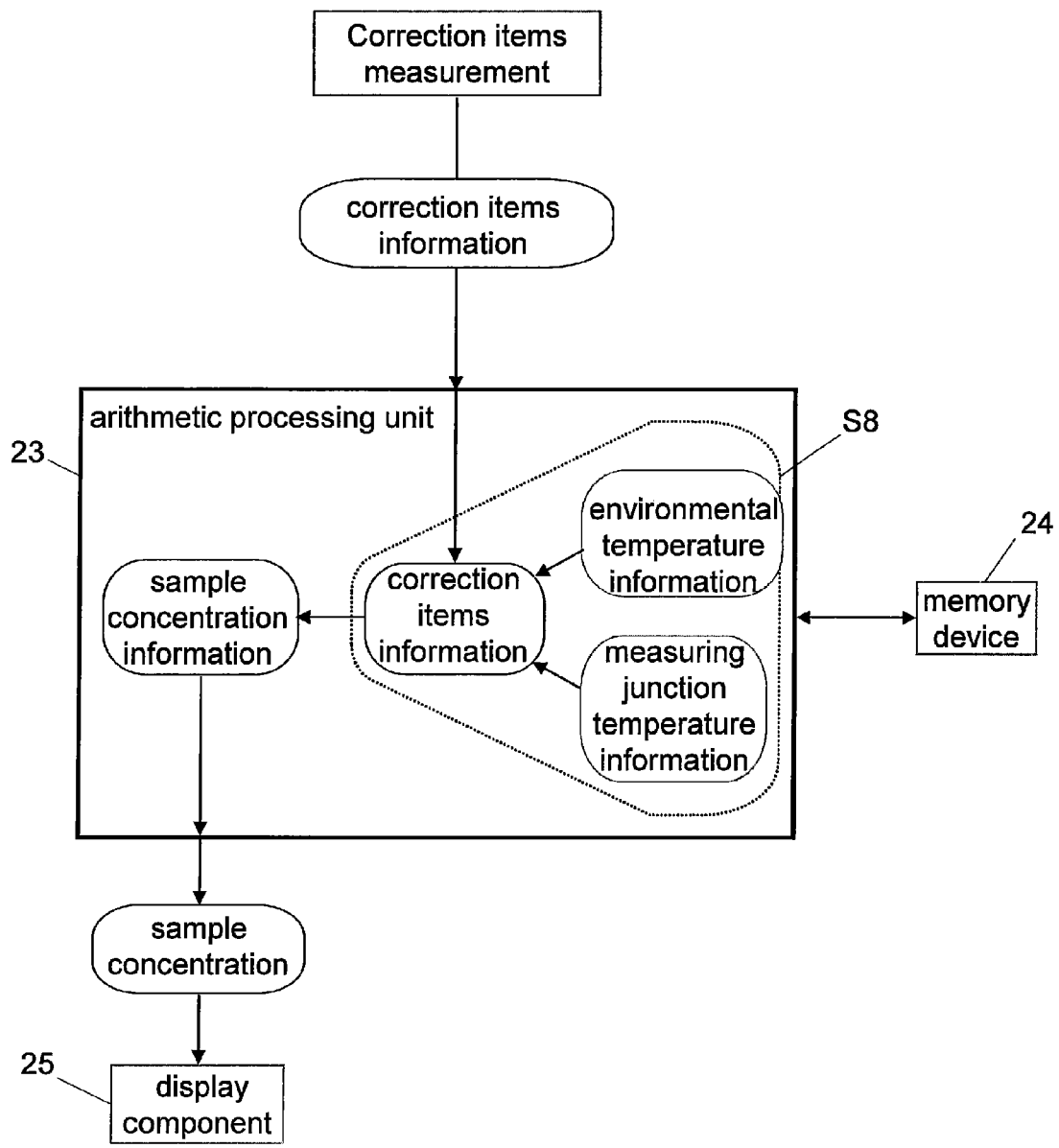
FIG. 7 is a simplified diagram of the measurement system steps in Embodiment 1 of the present invention.

FIGS. 6 and 7 are simplified diagrams of the various measurement steps and arithmetic processing in this temperature-compensating thermocouple analyzer. A simplified diagram of the various measurement steps and arithmetic processing was divided into FIGS. 6 and 7, but it should be noted that this is only to make it easier to understand the temperature compensation step S9 in the arithmetic component, and steps performed at the same time are shown as being divided.

If there is a temperature difference between the measuring junction 41 and the reference temperature junction 42 disposed as above, a thermoelectromotive force is outputted according to this temperature difference. A temperature information computation step S5 in which the environmental temperature and the measuring junction temperature are determined is then performed by means of a temperature difference measurement step S2 in which this thermoelectromotive force is measured, an environmental temperature measurement step S3 involving the use of the environmental temperature sensor 22, and a measuring junction temperature calculation step S4 in which the measuring junction temperature is calculated from the temperature difference information obtained in the temperature difference measurement step S2 and using the environmental temperature as a reference temperature. On the basis of the temperature information thus obtained, temperature compensation is performed for various correction items other than temperature and the analysis object concentration obtained in the specimen concentration measurement step (specimen measurement step) S1 discussed below.

Blood glucose value measurement using an analyzer with a temperature compensation function is carried out as follows, which is described according to the algorithm in FIG. 1, for example.

First, when the blood glucose value sensor 1 is placed in a dedicated measurement device 2, the system awaits sample introduction, and checking for sample introduction is begun. Meanwhile, the user pierces a fingertip or the like with a dedicated lancet or the like to draw blood. This blood is brought into contact with a blood supply opening at the distal end of the cavity 17 of the blood glucose value sensor 1 placed in the measurement device 2, and capillary action or assistance from a surfactant causes the blood to be introduced into the cavity 17.

The specimen concentration measurement step S1 is commenced when the detection electrode (not shown) that is part of the electrode system 14 detects that the required amount of blood has been introduced into the cavity 17. When the blood is introduced into the cavity 17, the measurement-use reagent 15 is dissolved, and a redox reaction begins with the glucose in the blood and an enzyme that uses glucose as a substrate. Here, when voltage is applied to the measurement electrode, which is part of the electrode system 14, current corresponding to the glucose concentration flows to the measurement electrode system 14. The specimen concentration measurement step S1 is performed in which the current value thus obtained is converted by a circuit into voltage, then converted into a digital signal, and converted by the arithmetic processing unit 23 into glucose concentration information, and this concentration information is stored in a memory device 24. Measurement is usually also performed for the various correction items simultaneously with or immediately before and after the specimen concentration measurement step S1. The environmental temperature measurement step S3 is then performed in which the environmental temperature information measured simultaneously with or before or after the measurement of the specimen is transferred from the environmental temperature sensor 22 to the arithmetic processing unit 23 and the environmental temperature is calculated.

The temperature difference measurement step S2 is also performed simultaneously with the specimen concentration measurement step S1. Specifically, the change in the thermoelectromotive force due to the temperature difference between the measuring junction 41 and the reference temperature junction 42 is measured, information about the change in temperature difference per unit of time for the two junctions, or information about the temperature difference within a specific length of time or at a certain point in time, is converted into a digital signal by the various circuits, and information about the temperature difference from the reference temperature junction is calculated by the arithmetic processing unit 23. Then, the measuring junction temperature calculation step S4 is performed by the arithmetic processing unit 23, in which the environmental temperature obtained in the environmental temperature measurement step S3 and stored in the memory device 24 is used as a reference temperature, and the temperature of the measuring junction 41 is calculated by matching this with the temperature difference information obtained in the temperature difference measurement step S2.

As discussed above, the obtained analysis object concentration information and measurement information for the various correction items undergo correction by temperature information. Specifically, the analysis object concentration information is subjected to the environmental temperature compensation step S6, in which correction is performed by the arithmetic processing unit 23 according to the environmental temperature information, and to the measuring junction temperature compensation step S7, in which correction is performed according to the measuring junction temperature information, and correction is also performed for the various correction items at a suitable timing before or after this. Naturally, as to these correction items that are affected by temperature, as shown in FIG. 7, accuracy can be further improved by performing the correction item temperature compensation step S8 in which temperature correction is performed by using environmental temperature information and measuring junction temperature information.

The glucose concentration is ultimately displayed on a display component 25, after the various corrections including temperature.

Figure 8:
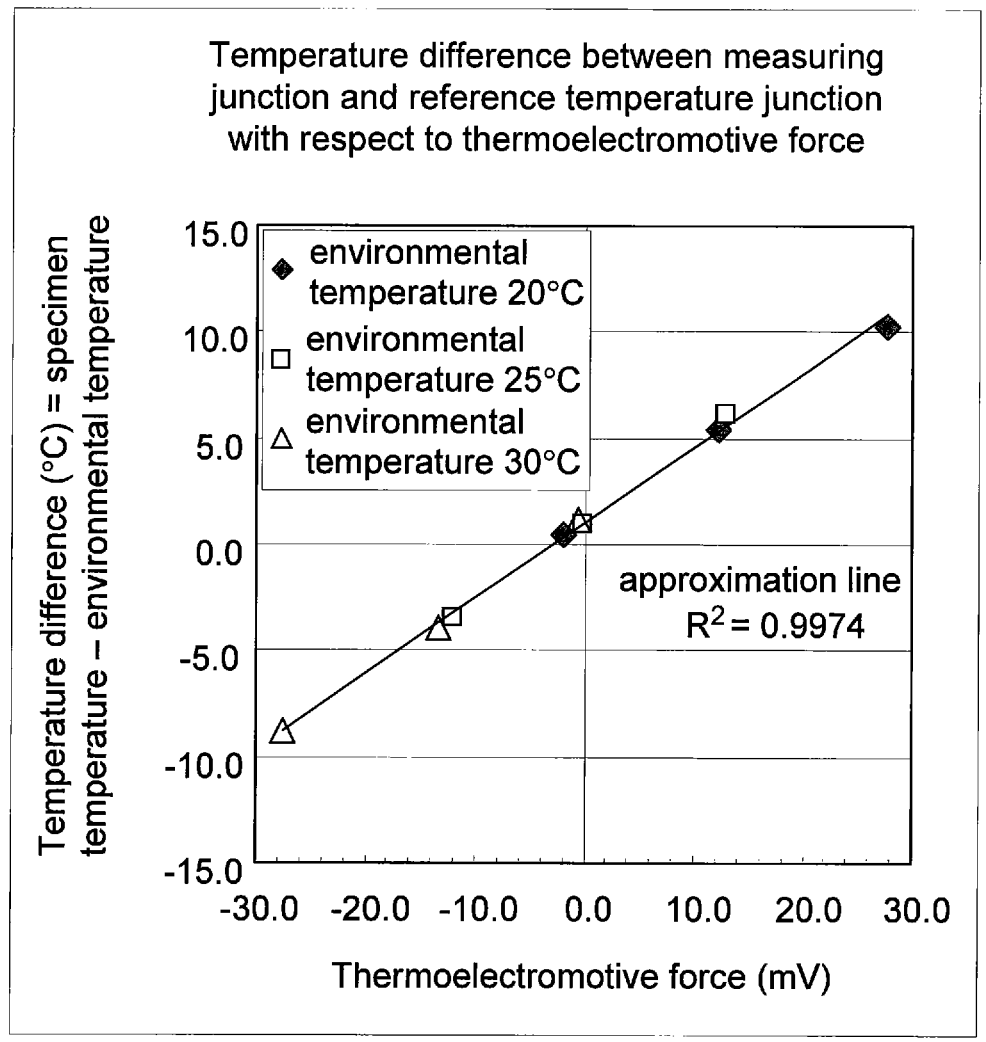
FIG. 8 is a graph of the relationship between temperature difference and thermoelectromotive force obtained in Embodiment 1 of the present invention.

Next, a blood glucose value sensor in which a thermocouple 16 was formed with the configuration shown in FIG. 3a was actually produced, and the relationship between the temperature difference between the measuring junction 41 and the reference temperature junction 42, and the thermoelectromotive force produced at the sensor/measurement device integrated thermocouple was measured with changing environmental temperature, the results of which are given in FIG. 8. The horizontal axis is the difference in the thermoelectromotive force with respect to a reference voltage of approximately 3.26 V, and the vertical axis is the temperature difference between the measuring junction 41 and the reference temperature junction 42 corresponding to the thermoelectromotive force. The term "reference voltage" here means the voltage applied ahead of time to a voltage measurement device to amplify and measure the negative thermoelectromotive force generated under conditions that the measuring junction 41 is lower than the reference temperature junction 42. In this embodiment, it can be seen that when a value under the reference voltage of 3.26 V was indicated, a negative thermoelectromotive force equivalent to this difference was generated. That is, the temperature of the measurement component must be lower than that of the reference temperature junction.

Measurement was conducted indoors at a constant temperature, with three different environmental temperature conditions employed: around 25° C., 30° C., and 35° C. As to the temperature of the sample, three spots were prepared so that the temperature would be constant near 20° C., 25° C., and 30° C., and measurements were made at the respective environmental temperatures.

As a result, as shown in FIG. 8, when the environmental temperature is held steady at 20° C., as the temperature of the sample is changed from 20° C. to 25° C. and then 30° C., the thermoelectromotive force generated at the thermocouple is −3.5 mV, 11.5 mV, and 26.5 mV, respectively, and when the environmental temperature is held steady at 25° C., as the temperature of the sample is changed from 20° C. to 25° C. and then 30° C., the thermoelectromotive force generated at the thermocouple is −15.5 mV, −2.5 mV, and 10 mV, respectively, and when the environmental temperature is held steady at 30° C., as the temperature of the sample is changed from 20° C. to 25° C. and then 30° C., the thermoelectromotive force generated at the thermocouple is −30.5 mV, −17 mV, and −3.5 mV, respectively. It is clear from these results that a positive thermoelectromotive force is generated with respect to the reference voltage if the temperature of the measuring junction 41 is high with respect to the reference temperature junction 42, and conversely, if the temperature is low, a negative thermoelectromotive force is outputted.

Also, as shown in FIG. 8, it can be seen that an approximation line for results under all conditions maintains linearity at all environmental temperatures, with $R^2=0.9974$. That is, no matter what the environmental temperature is, the relationship between the thermoelectromotive force and the temperature difference is obtained as data in a linear relationship approximated by a linear expression. The fact that this is obtained as a linear expression in which the calibration line is linear is extremely advantageous in the temperature difference measurement step S2 in which the temperature difference between the reference temperature junction 42 and the measuring junction 41 is calculated on the basis of the generated thermoelectromotive force. That is, with the integrated analyzer comprising the blood glucose value sensor 1 and the measurement device 2 in this Embodiment 1, no matter what the measurement environmental temperature, the value of the temperature difference between the two junctions can be computed with a single calibration line and without variance.

More specifically, when this data is stored as a calibration line in the memory device 24, then in the temperature difference measurement step S2 the obtained thermoelectromotive force can be converted into information about the temperature difference between the reference temperature junction 42 and the measuring junction 41 without being affected by the environmental temperature. The temperature difference information obtained in this way in the temperature difference measurement step S2 is further subjected to the measuring junction temperature calculation step S4, in which it is added up by the arithmetic processing unit 23 using the environmental temperature obtained in the environmental temperature measurement step S3 as a reference, so that the temperature of the measuring junction 41 is computed.

Then, on the basis of the measuring junction temperature information and the environmental temperature information thus obtained, the temperature compensation step S9 is performed, in which the corresponding environmental temperature compensation-use correction table or measuring junction temperature compensation-use correction table which is prospectively stored is referred to and, if correction is necessary, the analysis object concentration is subjected to temperature compensation. The temperature compensation step S9 also includes the correction item temperature compensation step S8 in which the various correction items are also subjected to temperature compensation.

Here, naturally, depending on the conditions of the temperature compensation, the compensation can be performed in both the environmental temperature compensation step S6 based on the environmental temperature and the measuring junction temperature compensation step S7 based on the measuring junction temperature, or just with temperature information from one or the other.

In the measuring junction temperature compensation step S7 based on the measuring junction temperature, measuring junction temperature information can be obtained as information about the temperature change in the measurement component 18 over time during measurement, and the temperature changes due to all internal and external thermal factors that affect the temperature of the measurement component 18 can be detected in real time. Of course, it is also possible to detect changes in the temperature of the measurement component linked to the temperature of the specimen when the specimen is introduced, or the peak temperature of the measurement component.

Figure 9:
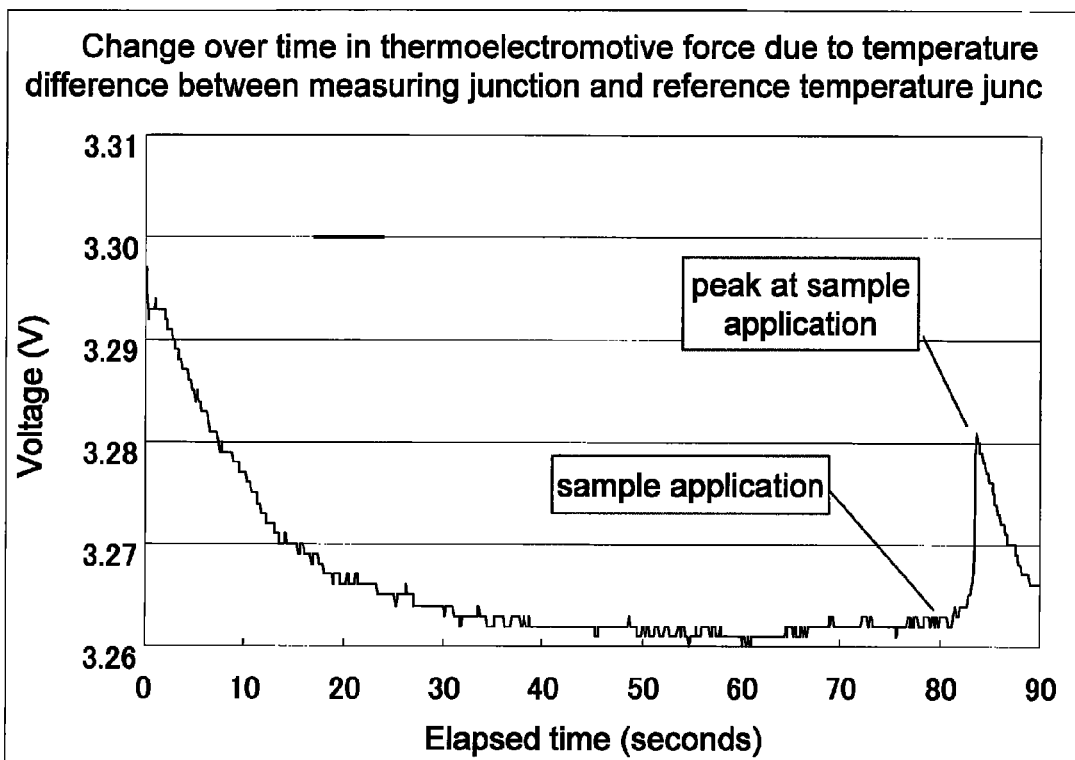
FIG. 9 is a graph of the change over time in temperature information for a measuring junction, obtained in Embodiment 1 of the present invention.

FIG. 9 is a graph of the measured values obtained by monitoring the change in thermoelectromotive force when a specimen whose temperature is higher than the environmental temperature is introduced into the cavity 17 for a while after the blood glucose value sensor 1 has been inserted into the measurement device 2 constituted as in this embodiment. The horizontal axis is the time elapsed since the blood glucose value sensor 1 was mounted in the measurement device 2, and the vertical axis is the thermoelectromotive force related to the temperature difference between the reference temperature junction 42 and the measuring junction 41. This shows the change over time in thermoelectromotive force related to the temperature difference between the measuring junction and the reference temperature junction.

As a result, as shown in FIG. 9, when the blood glucose value sensor 1 that has been stored indoors at an environmental temperature of 20° C. is inserted into the measurement device 2, the detected thermoelectromotive force is higher than the reference voltage, but gradually tapers off. This is because when the blood glucose value sensor 1 is taken out of its stored case and mounted in the measurement device 2, the fingertips come into contact with the blood glucose value sensor 1 and the heat of the fingertips is transferred to the blood glucose value sensor 1, so that the temperature of the measuring junction 41 of the blood glucose value sensor 1 is higher than the environmental temperature of the measurement device 2. The effect of fingertip temperature is also affected by the environmental temperature where the blood glucose value sensor 1 and the measurement device 2 are themselves stored.

After this, the thermoelectromotive force steadily drops, and after about 40 seconds have elapsed the voltage holds steady at about 3.262 V, but this means that since the reference voltage of the thermocouple is approximately 3.26 V in the prototype used in this embodiment, the voltage is the same as the reference voltage, that is, the temperature of the measuring junction 41 of the blood glucose value sensor 1 conforms to the temperature of the environment, until there is no longer any difference from the environmental temperature of the measurement device 2. Thus, in this embodiment, the difference between the temperature of the measuring junction 41, which indicates the temperature of the measurement component, and the reference temperature, which indicates the environmental temperature, can be detected in real time.

Next, a spot of 30° C. sample, which was 10° C. higher than the environmental temperature of 20° C., was placed in the cavity 17 of the blood glucose value sensor 1 about 80 seconds after the start of measurement. As a result, the detected value for thermoelectromotive force rose sharply to approximately 3.28 V. The peak of this temperature rise is calculated from the calibration line shown in FIG. 8 and found to be approximately 7° C., which is lower than the temperature of the applied specimen. The reason for this is surmised to be that the total amount of sample is too small with respect to the thermal capacity had by the blood glucose value sensor 1 or the environmental temperature, so the heat is absorbed before the measurement component 18 rises to the temperature of the specimen.

After the peak temperature rise has been reached, the temperature of the measurement component 18 gradually approaches the environmental temperature, just as with the fingertip temperature.

As shown in FIGS. 2, 3, and 5, with this embodiment, it probably can be understood that the specimen temperature can be measured directly by disposing the measuring junction 41 in the cavity 17. Also, due to high response speed of the thermocouple, it can be seen that the change in temperature around the measurement component 18 can be measured in real time by measuring the temperature in parallel with concentration measurement.

Naturally, the measuring junction temperature information used in the measuring junction temperature compensation step S7 does not require all of the change in temperature of the measurement component 18 over the course of measurement to be measured if the embodiment is optimized. That is, if the temperature change pattern of the measurement component 18 after specimen introduction, or the time over which it is possible to accurately detect the peak measurement component temperature is thoroughly scrutinized, then measurement may be performed for just as long as required after the start of measurement. Moreover, the temperature difference measurement step S2 can be concluded by obtaining measurement component temperature information for just a certain point in time after the start of measurement.

Thus, accurate temperature compensation of an analysis object can be achieved, which was impossible with conventional environmental temperature compensation alone. Therefore, this embodiment makes it possible to accomplish accurate measurement in which the effect on temperature by measurement conditions is kept to a minimum.

Also, the data for the prototype in Embodiment 1, namely, the thermocouple that is used, the resistance thereof, the amount of amplification by the amplifier, the thermoelectromotive force, and the linearity of the calibration line obtained from this, will vary greatly, so it should be noted again that the calibration line obtained here is nothing but one aspect of Embodiment 1.

Embodiment 2

Figure 10:
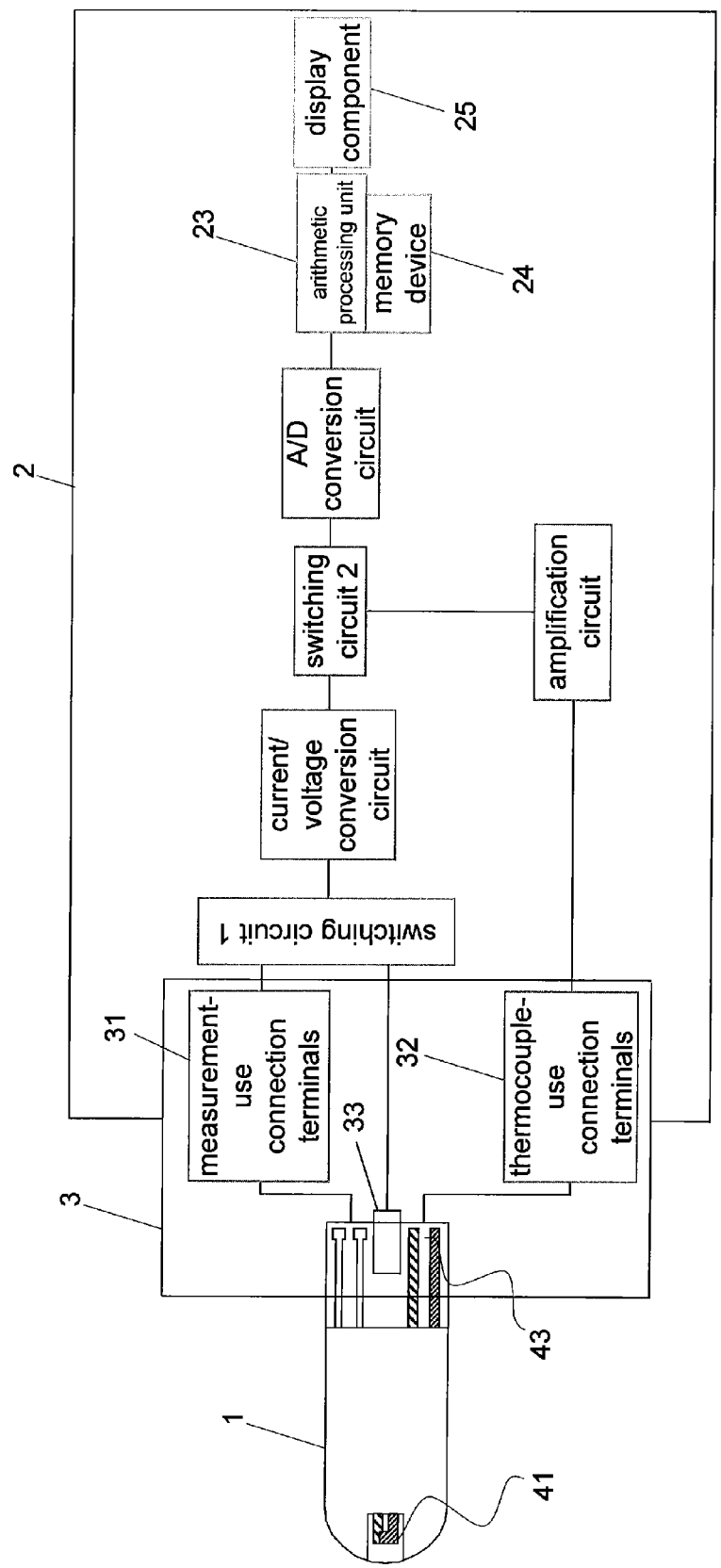
FIG. 10 is a simplified diagram of an analyzer in Embodiment 2 of the present invention.
Figure 11:
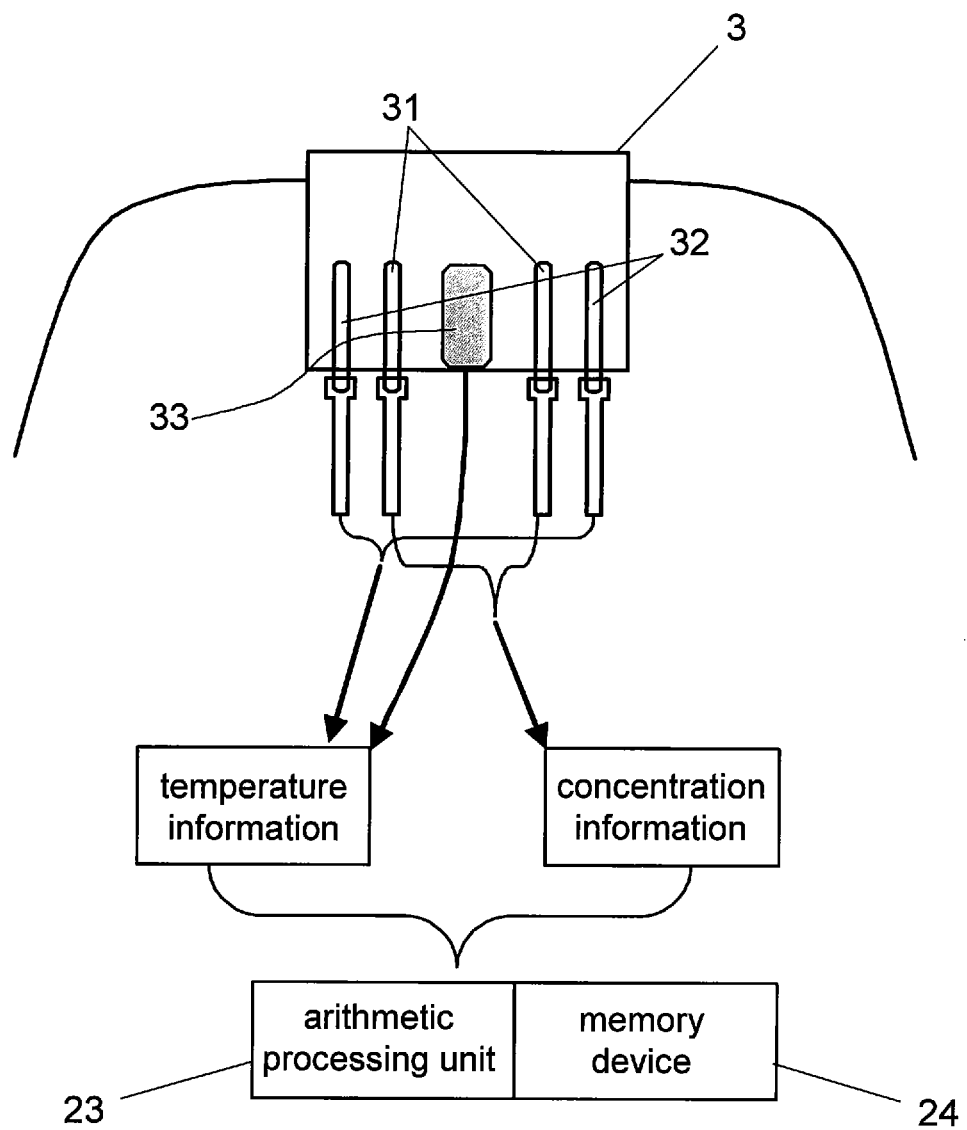
FIG. 11 is a simplified diagram of a measurement device in Embodiment 2 of the present invention.
Figure 12:
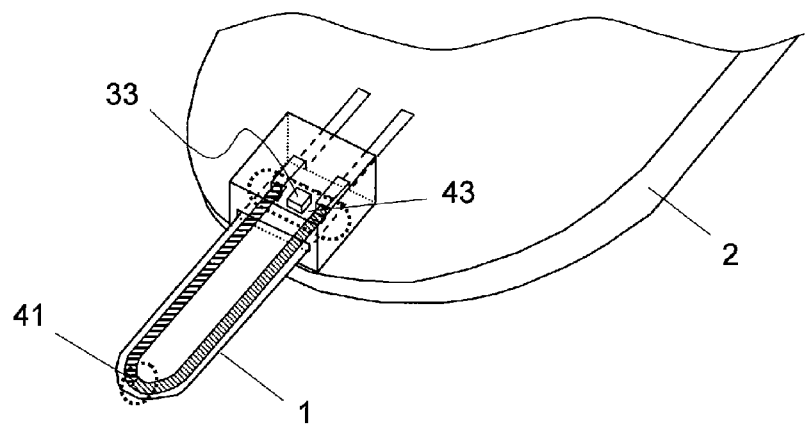
FIGS. 12a, 12b, and 12c are a simplified diagram of the configuration of a temperature measurement system in Embodiment 2 of the present invention.
Figure 12:
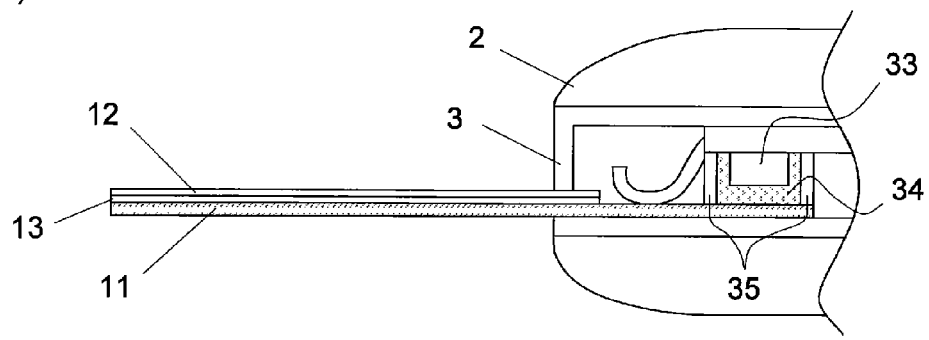
Figure 12:
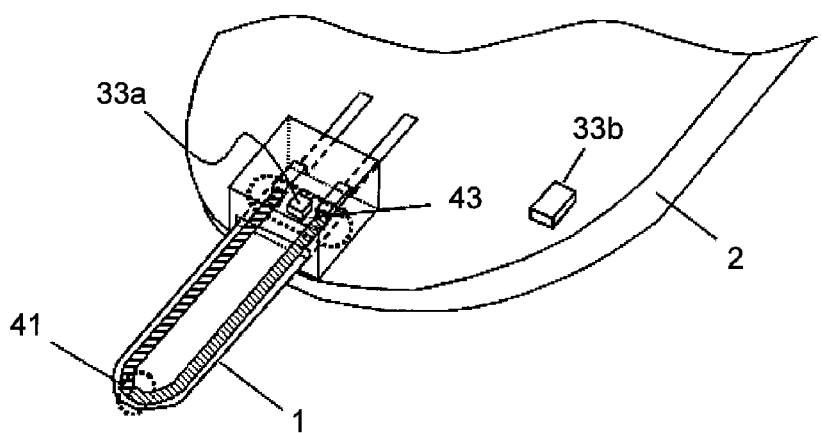
Figure 13:
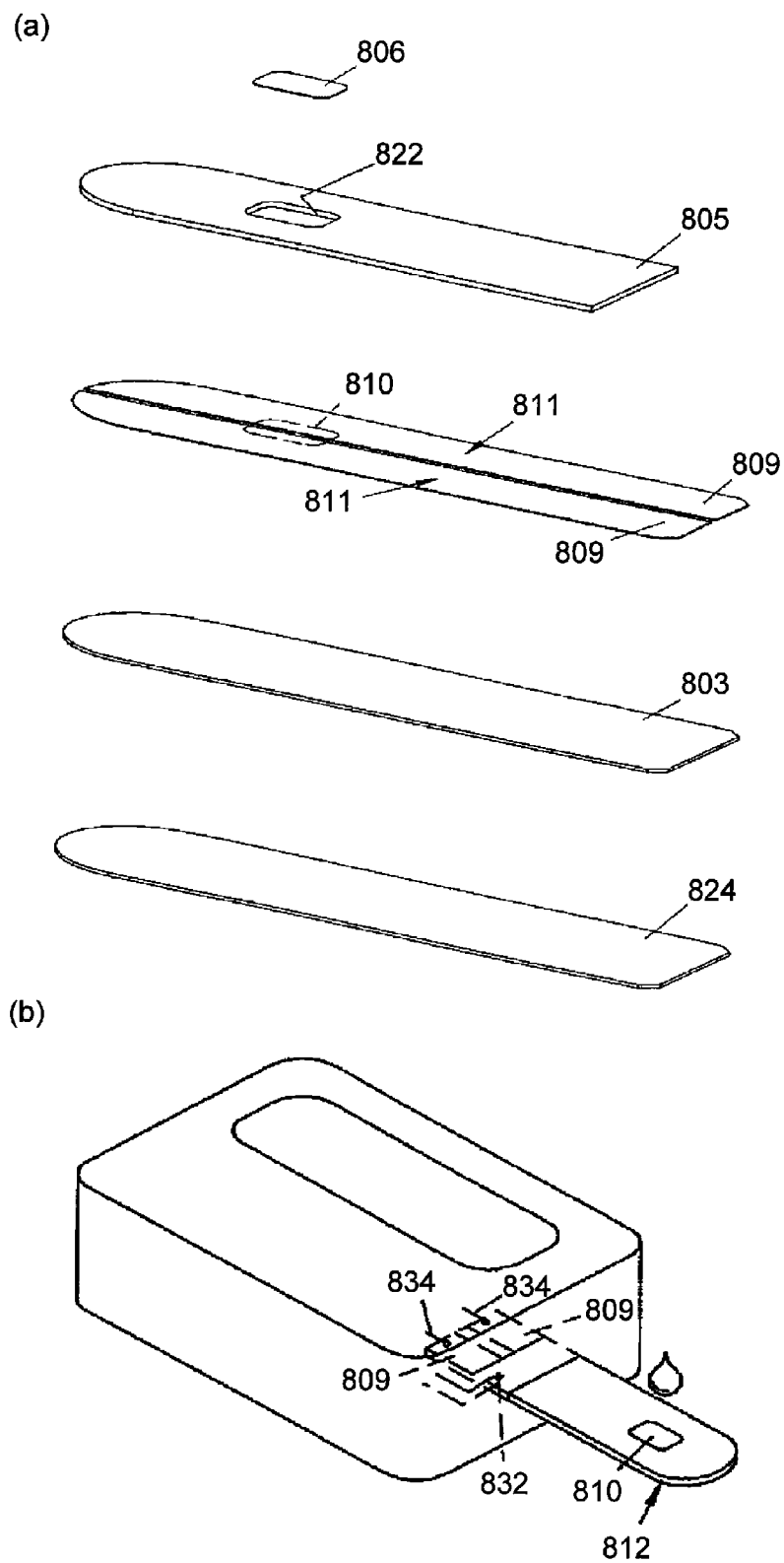
FIGS. 13a and 13b are an exploded view of a conventional sensor and a simplified diagram of a measurement device in which a sensor is inserted.
Figure 14:
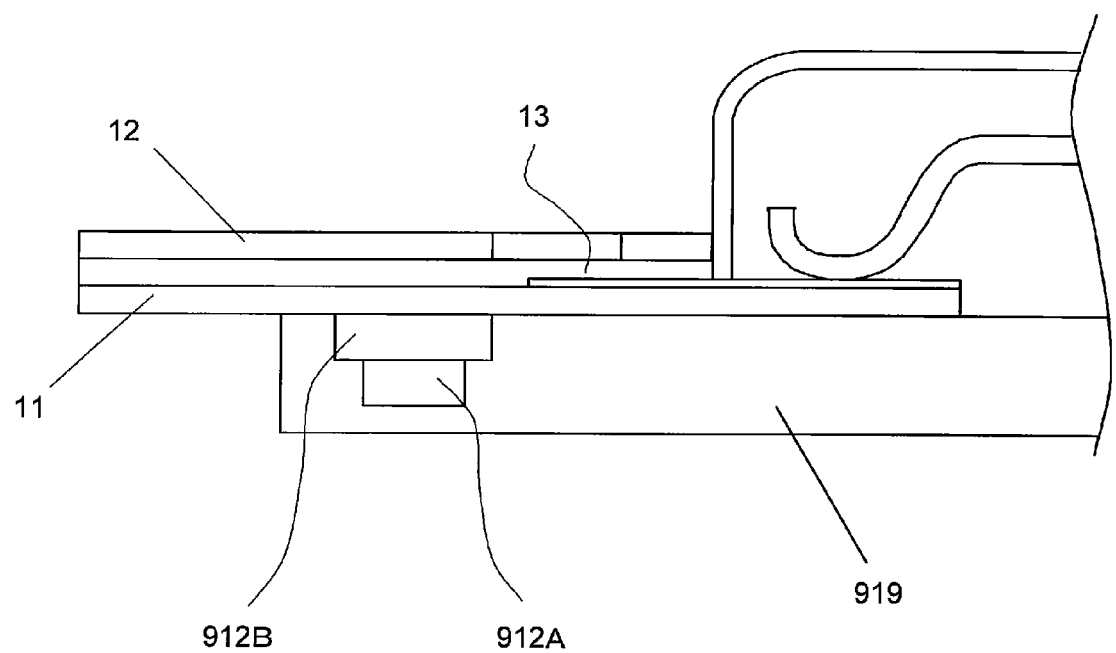
FIG. 14 is a cross section of the main components of a measurement device in which a conventional sensor is inserted.

Next, the temperature-compensating analyzer (measurement device) and method thereof (method for measuring an analysis object) of Embodiment 2 will be described through reference to FIGS. 10 to 12. Those elements that are the same as in Embodiment 1 will be numbered the same, and will be treated as being included in Embodiment 2 as well. FIGS. 10 to 12 are of course nothing more than an aspect of the present invention, and this embodiment is not limited to or by these.

As shown in FIGS. 10, 11, and 12, an integrated temperature-compensating thermocouple analyzer comprising the blood glucose value sensor 1 and the measurement device 2 in Embodiment 2 differs from Embodiment 1 in the configuration of the thermocouple, the position of the reference temperature junction 42, and the configuration of the environmental temperature sensor 22 that measures the reference temperature.

In Embodiment 2, the thermocouple, which is part of a temperature correcting circuit, ends only on the blood glucose value sensor 1, and the second wires 21a and 21b disposed in the measurement device 2 in Embodiment 1 are omitted. At the same time, the material of the thermocouple-use connection terminals 32 disposed in the sensor holder 3 that removably holds the blood glucose value sensor 1 is different from the material of the thermocouple. Accordingly, in Embodiment 2, the ends of the thermocouples 16a and 16b on the blood glucose value sensor 1 act as a reference temperature junction 43, and if there is a temperature difference between this reference temperature junction 43 and the measuring junction 41, a thermoelectromotive force is generated between the ends of the thermocouples 16a and 16b. That is, as discussed above, the thermocouple ends at just the thermocouples 16a and 16b on the blood glucose value sensor 1.

In addition, as shown in FIGS. 12a and 12b, the environmental temperature sensor 22 is incorporated as a reference temperature junction sensor 33, and is incorporated so as to come into contact with the reference temperature junction 43 (or nearby it) on the mounted blood glucose value sensor 1 inside the sensor holder 3 that removably holds the blood glucose value sensor 1, with this contact being either direct or indirect via the provision of a thermally conductive layer 34, and this sensor measures the temperature of the reference temperature junction 43. Examples of reference temperature junction sensor 33 include a thermistor, a temperature sensing resistor, an IC temperature sensor, and a radiation thermometer.

As shown in FIG. 12c, for example, the reference temperature junction sensor 33 may comprise a third temperature sensor 33a for acquiring the reference temperature of the thermocouples, and a fourth temperature sensor 33b for acquiring the environmental temperature of the measurement device 2, with these two being provided separately.

In this case, in a preferable configuration, as shown in FIG. 12b, the thermally conductive layer 34 is provided to afford indirect contact. This creates a structure in which the reference temperature junction sensor 33 is enveloped by the thermally conductive layer 34, so the temperature of the reference temperature junction 43 is transferred more quickly, and also serves to protect the reference temperature junction sensor 33 from the physical effect of inserting and removing the blood glucose value sensor 1.

There are no particular restrictions on the material of the thermally conductive layer 34, but the thermal conductivity thereof is preferably at least 50 W/m·K, for example, and more preferably at least 100 W/m·K, and even more preferably at least 200 W/m·K.

As shown in FIG. 12b, in a more preferable configuration of the reference temperature junction sensor 33, the portion of the thermally conductive layer 34 that is not in contact with the reference temperature junction 43 is covered with a non-thermally conductive substance 35, so the temperature of the reference temperature junction 43 can be transferred more reliably to the reference temperature junction sensor 33 without the environmental temperature of the nearby area having any effect.

There are no particular restrictions on the material of the non-thermally conductive substance 35, but the thermal conductivity thereof is preferably no more than 20 W/m·K, for example, and more preferably no more than 1 W/m·K, and even more preferably no more than 0.2 W/m·K.

The reference temperature junction sensor 33 is used instead of the environmental temperature sensor 22 in Embodiment 1 above. That is, the various temperature information used to carry out the temperature compensation step S9 is computed in the temperature information computation step S5 according to the algorithm in FIGS. 1, 6, and 7, just as in Embodiment 1, by using the temperature information measured by the reference temperature junction sensor 33 as the environmental temperature information.

The information about measurements of the analysis object via the temperature compensation step S9 can be obtained as accurate measurement results, and the effect of temperature due to measurement conditions can be kept to a minimum just as in Embodiment 1.

The analysis object measurement method in this embodiment is a method for measuring an analysis object in which a specific component in an analysis object is measured with a biosensor system comprising a holder for holding the analysis object, an electrode system for measuring the analysis object, and a thermocouple formed by joining at least two dissimilar substances, said method comprising a specimen measurement step, a temperature information computation step, and a temperature compensation step. In the specimen measurement step, a specific component is measured in a spot of the analysis object that has been applied to the holder. In the temperature information computation step, temperature information is acquired using the thermocouple. In the temperature compensation step, the value measured in the specimen measurement step is corrected on the basis of the temperature information.

The measured values in the specimen measurement step include, for example, concentration or volume, mass, various correction items, and so forth, and the temperature compensation step involves correcting these measured values on the basis of temperature information.

With the above method, the characteristics of a thermocouple are utilized to perform temperature measurement, which allows the measured values for an analysis object to be corrected accurately.

As a result, the effect of temperature due to measurement conditions can be kept to a minimum, and a specific component in the analysis object can be measured accurately.

With the method for measuring an analysis object of this embodiment, the temperature information computation step has a temperature difference measurement step, an environmental temperature measurement step, and a measuring junction calculation step. The temperature difference measurement step involves measuring the temperature difference between a measuring junction that is one of the junctions of the thermocouple and a reference temperature junction that is the other junction. The environmental temperature measurement step involves measuring the temperature of the reference temperature junction or its nearby area as a reference temperature/environmental temperature. The measuring junction calculation step involves computing temperature information for the measuring junction from the temperature difference information obtained in the temperature difference measurement step.

Here, the "temperature of the nearby area of the reference temperature junction" refers to an area within a range in which there is no temperature difference from the reference temperature junction temperature.

Because of the properties of a thermocouple, the thermoelectromotive force is usually determined by the temperature difference between two points: the measuring junction and the reference temperature junction. Accordingly, no matter where on the thermocouple the temperature is transferred due to another factor, as long as the temperature of the reference temperature junction is measured, the temperature of the measuring junction can be found from the thermoelectromotive force that is measured.

Consequently, it is possible to accurately calculate the temperature of the measurement region where the measuring junction is disposed. As a result, it is possible to accurately correct the concentration, for example, which is one of the measured values for the analysis object that is measured at the specimen measurement step.

With the method for measuring an analysis object of this embodiment, the environmental temperature measurement step and the temperature difference measurement step are performed in parallel with the specimen measurement step.

The reason the temperature change can be measured in parallel with the specimen measurement step in the environmental temperature measurement step and the temperature difference measurement step here is that neither the thermocouple or the mechanism that measures the environmental temperature is affected by the measurement of a specimen, and is also related to the fast response of a thermocouple.

Consequently, the change in temperature during measurement due to all internal and external factors that affect the temperature of the measurement region can be detected. Accordingly, the peak temperature can also be detected from the pattern of change, and this affords more accurate temperature compensation of the analysis object.

With the method for measuring an analysis object of this embodiment, the environmental temperature measurement step and the temperature difference measurement step involve clocking from a point in time when measurement preparations are complete, or from the point when the specimen measurement step was started until a predetermined length of time has elapsed.

Consequently, data for just the length of time necessary for temperature compensation can be efficiently extracted. Alternatively, if the reaction system has been thoroughly inspected, just the temperature at a predetermined timing may be measured.

As a result, by measuring for just the required length of time or at the required timing, the information, power consumption, and steps entailed by measuring the temperature of an analysis object can be reduced. Meanwhile, more accurately temperature compensation can be performed by acquiring temperature information beyond the measurement time for the analysis object.

With the method for measuring an analysis object of this embodiment, the temperature compensation step includes an environmental temperature compensation step of correcting the measured value on the basis of the environmental temperature measured in the environmental temperature measurement step.

This makes it possible to accommodate situations in which temperature compensation can be performed more accurately by correcting the measured value on the basis of the environmental temperature, rather than the temperature of the measuring junction.

With the method for measuring an analysis object of this embodiment, the environmental temperature compensation step involves correcting the measured value on the basis of a correction table containing correction amounts corresponding to the environmental temperature.

Consequently, it is possible to correct the measured value easily on the basis of the environmental temperature.

With the method for measuring an analysis object of this embodiment, the temperature compensation step further includes a measuring junction temperature compensation step of correcting the measured value on the basis of the measuring junction temperature information calculated in the measuring junction temperature calculation step.

Consequently, even if the temperature of the analysis object during measurement is different from the environmental temperature when the calibration line was set, the measured value can be corrected on the basis of the measuring junction temperature information calculated in the measuring junction temperature calculation step. Thus, situations can be accommodated in which temperature compensation can be performed more accurately by correcting the measured value on the basis of the measuring junction temperature, rather than the environmental temperature.

With the method for measuring an analysis object of this embodiment, the measuring junction temperature compensation step involves correcting the pattern of change of the measuring junction temperature, or the peak temperature, or the temperature at a predetermined point in time.

Consequently, correction is possible according to the ideal format of temperature information for the targeted analysis object.

With the method for measuring an analysis object of this embodiment, the measuring junction temperature compensation step involves correcting the measured value on the basis of a correction table containing correction amounts corresponding to the measuring junction temperature information.

Consequently, it is possible to correct the measured value easily on the basis of the measuring junction temperature.

With the method for measuring an analysis object of this embodiment, the temperature compensation step further includes a correction item temperature compensation step of correcting each correction item affected by temperature out of the various correction items obtained in the specimen measurement step, on the basis of the environmental temperature and/or the measuring junction temperature.

The "various correction items" referred to here are elements other than temperature for correcting the measured values of the analysis object, and include hematocrit value correction, correction of interfering substances, etc.

Consequently, just as with the analysis object, the various correction items can also be corrected for the effect of environmental temperature or the temperature of the measurement region, or both, so the measured values for the analysis object can be acquired more accurately.

With the method for measuring an analysis object of this embodiment, the correction item temperature compensation step involves correcting the various correction items on the basis of a correction table containing correction amounts corresponding to the environmental temperature and/or the measuring junction temperature.

Consequently, it is possible to correct the measured value easily on the basis of the environmental temperature and the measuring junction temperature information.

With the method for measuring an analysis object of this embodiment, the temperature calculated in the measuring junction temperature calculation step is used as the temperature inside the holder for holding the analysis object.

Consequently, it is possible to measure the raw temperature of the analysis object being measured, and the measured values can be corrected more accurately.

With the method for measuring an analysis object of this embodiment, the temperature calculated in the measuring junction temperature calculation step is used as the temperature of the measurement component serving as the measurement region between the electrodes in the measurement of the analysis object.

Consequently, it is possible to measure the raw temperature of the region of the analysis object that is actually being measured, and the measured values can be corrected more accurately.

With the method for measuring an analysis object of this embodiment, the temperature compensation step is performed when the environmental temperature or the temperature difference calculated in the temperature difference measurement step indicates a specific value.

Consequently, the above-mentioned correction can be performed only on measured values that are expected to have low accuracy.

The biosensor of this embodiment comprises a holder, an electrode system, and a thermocouple. The holder holds an analysis object. The electrode system measures the analysis object. The thermocouple is formed by joining at least two dissimilar substances.

Consequently, it is possible to acquire temperature information and measure an analysis object with a biosensor.

With the biosensor of this embodiment, the junction of dissimilar substances is a measuring junction of a thermocouple. The measuring junction is disposed inside the holder for holding the analysis object.

Consequently, it is possible to measure the temperature of an analysis object directly. Making a correction on the basis of a temperature acquired in this way keeps the effect of temperature due to measurement conditions to a minimum, and allows an accurate measured value to be provided for a specific component of the analysis object.

With the biosensor of this embodiment, the junction of dissimilar substances is a measuring junction of a thermocouple. The measuring junction is disposed near the holder.

Consequently, when the measurement of the analysis object and the acquisition of temperature information by the thermocouple has an adverse effect on each other or on one or the other, the temperature is measured at as close as possible to the temperature of the measurement component. Making a correction on the basis of a temperature acquired in this way keeps to a minimum the effect of temperature due to the measurement conditions, and allows an accurate measured value to be provided for a specific component of the analysis object.

With the biosensor of this embodiment, the measuring junction is disposed upstream from the electrode system with respect to the flow of the placed drop of analysis object.

Consequently, the wiring of the thermocouple and the electrode system can be facilitated.

With the biosensor of this embodiment, both ends that are part of the thermocouple are in locations that come into contact with thermocouple-use connection terminals provided to a measurement device that measures the analysis object drop placed in the holder, in mounting to this measurement device.

Consequently, when the biosensor is actually mounted to a measurement device that is the key component that performs measurement and computation, an environment can be provided that takes advantage of the inherent performance of the thermocouple and the measurement device.

With the biosensor of this embodiment, the substance that makes up the thermocouple is composed of either a metal, an alloy, or a semiconductor, or a combination of these.

Consequently, it is possible to select the material as dictated by the application conditions.

With the biosensor of this embodiment, the holder has a cavity structure, and is formed by affixing a first substrate, a second substrate, and a third substrate together so that the analysis object will be supplied by capillary action.

Consequently, capillary action can be utilized to guide the analysis object into the measurement component. Thus, various measurements of the introduced analysis object can be performed in the measurement component.

With the biosensor of this embodiment, the holder is formed by affixing two substrates together by the three-dimensional molding of the substrates.

Consequently, the sensor is made up of fewer members, and the manufacturing processing can be simplified.

With the biosensor of this embodiment, the electrode system and the thermocouple are both provided on the same substrate.

Consequently, in producing and machining the electrode system and thermocouple, they can be machined simultaneously on a single substrate, or can be centralized thereon.

With the biosensor of this embodiment, the electrode system has its electrodes formed on mutually opposing substrates, with one electrode system and the thermocouple both formed on the same substrate.

Consequently, the electrode system and the thermocouple are disposed over a wider area, which affords greater latitude in wiring to suit the intended application.

With the biosensor of this embodiment, the electrode system and the thermocouple are formed on mutually opposing substrates or substrate side faces.

Consequently, the electrode system and the thermocouple are independent of each other, which affords even greater latitude in wiring, and makes it possible, for example, to dispose the measuring junction directly over the measurement component.

With the biosensor of this embodiment, one of the substances that form the thermocouple utilizes the wiring of the electrode system, or is made of the same material as the electrode system.

This imparts the function of a thermocouple to the electrode used for measuring a specific component, or to the electrode used for measuring correction items.

Consequently, whereas three different materials (the electrode material, the thermocouple material 1, and the thermocouple material 2) would otherwise be necessary, using an electrode/thermocouple material 1 and a thermocouple material 2 reduces the number of manufacturing steps and also lowers costs.

With the biosensor of this embodiment, the thermocouple and the electrode system are formed on the substrates by sputtering, vapor deposition, or printing.

Consequently, it is possible to use the manufacturing method that is best suited to producing an electrode system and a thermocouple.

With the biosensor of this embodiment, the electrode system is such that an electroconductive layer is formed over all or part of at least one face among the first substrate, the second substrate, and the third substrate, and slits are provided to form an electrode pattern.

Consequently, the electrode pattern can be easily modified by changing the drawing model as necessary.

With the biosensor of this embodiment, the electrode system is such that an electrode pattern is formed by masking over all or part of at least one face among the first substrate, the second substrate, and the third substrate.

Consequently, the electrode system can be produced at just the required place, so when a noble metal or the like is used for the electrode system, the amount in which it is used can be reduced. Also, the material of the electrode system can be recovered from the masked member by using one of the various methods that have already been developed.

With the biosensor of this embodiment, the electrode is such that a pattern is formed by masking over all or part of at least one face among the first substrate, the second substrate, and the third substrate.

Consequently, it is possible to produce the thermocouple without overlapping the electrode system or any place other than the measuring junction.

With the biosensor of this embodiment, all or part of the surface of the holder is covered with a surfactant.

Consequently, a hydrophilic side wall is formed, so the analysis object can be introduced more efficiently into the holder (the cavity, etc.).

With the biosensor of this embodiment, the electrode system has at least a working electrode and a counter electrode.

Consequently, various targeted components can be quantified by applying an appropriate voltage to the working electrode and the counter electrode and detecting the redox current produced from the targeted components.

With the biosensor of this embodiment, a measurement reagent for oxidizing or reducing a specific target component is provided to the holder.

Consequently, the targeted components can be quantified by applying voltage to the counter electrode and the working electrode used for measuring the specific components (part of the electrode system), detecting the redox current produced from the targeted components and a measurement-use reagent, and converting the current value into a targeted component content.

The biosensor of this embodiment is used disposably.

Consequently, even when an infectious analysis object is measured, measurements can be made any number of times with a single measurement device by replacing just the biosensor each time. This also lowers the cost borne by the user.

The measurement device of this embodiment comprises a holder for holding an analysis object, an electrode system for measuring the analysis object, and a thermocouple formed by joining at least two substances and that outputs a temperature difference as a thermoelectromotive force, or a sensor holder to which can hold a removable biosensor comprising a part thereof. The sensor holder has measurement-use connection terminals that are in contact with the electrode system in the biosensor and are used to take off signals required for measuring the specific component, and thermocouple-use connection terminals that are in contact with the thermocouple in the biosensor and are used to take off the thermoelectromotive force signals.

Consequently, it is possible to perform the electrochemical operation required for various measurements, such as electrically connecting the thermocouple and the electrode system on the biosensor, applying voltage, and reading the current value.

With the measurement device of this embodiment, the thermocouple-use connection terminal is made of the same material as the thermocouple in the biosensor with which it is in contact, or is an compensating lead material corresponding to the material of the thermocouple.

Consequently, the reference temperature junction of the thermocouple can be extended to the thermocouple-use connection terminals.

With the measurement device of this embodiment, the thermocouple-use connection terminals are both made of the same material, which is different from the materials constituting the thermocouple.

Consequently, the ends of the thermocouple on the biosensor can be treated as the reference temperature junction of the thermocouple.

With the measurement device of this embodiment, the surface of the thermocouple-use connection terminals has undergone metal plating.

Consequently, ends that function to hold the biosensor will have improved durability with respect to the plugging and unplugging of the biosensor.

The measurement device of this embodiment comprises a thermocouple provided to the biosensor, and a second thermocouple that forms a biosensor/measurement device integrated thermocouple via the thermocouple-use connection terminals.

Consequently, the reference temperature junction of the thermocouple is extended to the ends of the second thermocouple (second wiring) inside the measurement device, and it is possible to measure the temperature difference between the inside of the measurement device and the measuring junction on the biosensor.

With the measurement device of this embodiment, the ends of the second thermocouple disposed in the measurement device are disposed as close as possible.

Consequently, the temperature difference between the ends of the second thermocouple serving as the reference temperature junction can be eliminated as much as possible.

With the measurement device of this embodiment, the ends of the second thermocouple are a reference temperature junction of a thermocouple that is integrated with the biosensor, and the measurement device comprises an environmental temperature sensor for acquiring the reference temperature/environmental temperature of the reference temperature junction or of the integrated thermocouple that is nearby.

Consequently, the reference temperature/environmental temperature can be measured at the reference temperature junction of an integrated thermocouple.

As a result, it is possible to calculate the temperature of the measuring junction according to the temperature difference information of the thermocouple.

With the measurement device of this embodiment, the environmental temperature sensor individually has a first temperature sensor for acquiring the reference temperature of the integrated thermocouple, and a second temperature sensor for acquiring the environmental temperature of the measurement device.

Consequently, by individually measuring the reference temperature and the environmental temperature it is possible to acquire suitable temperature information for each.

The measurement device of this embodiment comprises a function of measuring the temperature of the measuring junction, integrally with the thermocouple provided to the biosensor.

Consequently, the effect of temperature due to measurement conditions can be kept to a minimum by means of the temperature information of the measurement component, and a specific component of the analysis object can be accurately measured.

With the measurement device of this embodiment, the thermocouple-use connection terminals are such that the ends of the thermocouple on the biosensor are disposed as close as possible.

Consequently, the temperature difference between the ends can be kept to a minimum even with a configuration in which the thermocouple ends on the biosensor serve as the reference temperature junction of the thermocouple.

The measurement device of this embodiment further comprises a reference temperature junction temperature sensor that is disposed in contact with the ends of the reference temperature junction of the thermocouple disposed in the biosensor, or nearby these ends, and is for acquiring the reference temperature/environmental temperature of the thermocouple.

Consequently, the reference temperature junction temperature can be measured at the reference temperature junction of the thermocouple on the biosensor.

As a result, it is possible to calculate the temperature of the measuring junction according to the temperature difference information of the thermocouple.

With the measurement device of this embodiment, the reference temperature junction temperature sensor individually has a third temperature sensor for acquiring the reference temperature of the thermocouple disposed in the biosensor, and a fourth temperature sensor for acquiring the environmental temperature of the measurement device.

Consequently, by individually measuring the reference temperature and the environmental temperature it is possible to acquire suitable temperature information for each.

The measurement device of this embodiment further comprises the above-mentioned biosensor.

Consequently, a thermocouple is formed by a biosensor and a measurement device, and the thermocouple characteristics discussed above can be utilized to directly measure the temperature of an analysis object.

As a result, the effect of temperature due to measurement conditions can be kept to a minimum, and a specific component of the analysis object can be accurately measured.

The measurement device of this embodiment further comprises an arithmetic processing unit for calculating temperature information at the measuring junction, which is one of the junctions of the thermocouple formed in the biosensor, using as a reference the reference temperature/environmental temperature or the reference temperature.

Here, the arithmetic processing unit calculates temperature information at the measuring junction on the basis of the temperature of the reference temperature junction measured by the reference temperature junction sensor, or the temperature of the reference temperature junction measured by the environmental temperature sensor.

With the measurement device of this embodiment, the arithmetic processing unit corrects the measured value that is the result of measuring the specific component in the drop of analysis object placed in the holder, on the basis of the reference temperature/environmental temperature or the reference temperature.

The measured value referred to here includes, for example, concentration or volume, mass, various correction items, and so forth.

Consequently, even if the temperature when the analysis object is measured is different from the temperature when the calibration line for calculating the measured value was set, the measured value can still be corrected on the basis of the temperature measured by the environmental temperature sensor or the reference temperature junction sensor.

With the measurement device of this embodiment, the arithmetic processing unit corrects the measured value that is the result of measuring the specific component in the drop of analysis object placed in the holder, on the basis of the temperature information at the measuring junction.

The measured value referred to here includes, for example, concentration or volume, mass, various correction items, and so forth.

Consequently, even if the temperature when the analysis object is measured is different from the temperature when the calibration line for calculating the measured value was set, the measured value can still be corrected on the basis of the temperature information for the measuring junction With the measurement device of this embodiment, the arithmetic processing unit performs temperature correction for the various correction items with respect to the result of measuring the drop of analysis object placed in the holder, on the basis of the reference temperature/environmental temperature or the reference temperature, and/or the temperature information at the measuring junction, and corrects the measured value on the basis of these temperature-corrected correction items.

The various correction items referred to here are elements for correcting measured values, such as concentration, and include all items that are affected by temperature, such as hematocrit value correction, correction of interfering substances, etc.

Consequently, the effect of temperature can be excluded for the various correction items that affect the measured values, so the measured values for the analysis object can be corrected more effectively, and these measured values can be more accurate.

The measurement device of this embodiment further comprises a current/voltage conversion circuit, an amplifier circuit, an A/D converter circuit, and a memory device. The current/voltage conversion circuit converts the current values measured by the electrode system and the environmental temperature sensor or the reference temperature junction sensor into voltage. The amplifier circuit amplifies the thermoelectromotive force in the biosensor. The A/D converter circuit converts the voltage converted by the current/voltage conversion circuit or the amplifier circuit into a digital signal. The memory device records the various measured values and the various temperature information converted into a digital signal by the A/D converter circuit. The arithmetic processing unit computes the various measured values and the various temperature information from the digital signals, and corrects the various measured values using the various temperature information according to various conditions.

With the measurement device of this embodiment, the memory device has a correction table used by the arithmetic processing unit for correcting the various correction items or the measured values corresponding to the environmental temperature or the reference temperature and the measuring junction temperature.

Consequently, the measured values for the various correction items can be corrected easily by using this correction table.

With the present invention, the temperature inside a holder that holds an analysis object can be measured directly, so more accurate temperature compensation of the analysis object is possible, and a specific component of the analysis object can be measured accurately.

The invention claimed is:
1. A measurement device, comprising:
a sensor holder;
a biosensor, the biosensor being removable connected to the sensor holder;
a cavity in the biosensor for holding an analysis object;
an electrode system in the biosensor for measuring the analysis object; and
a thermocouple or a part thereof formed by joining at least two substances and that outputs a temperature difference as a thermoelectromotive force,
wherein the sensor holder has measurement-use connection terminals that are in contact with the electrode system in the biosensor and are used for communicating signals required for measuring the specific component, and thermocouple-use connection terminals that are in contact with the thermocouple in the biosensor and are used for communicating the thermoelectromotive force signals.

2. The measurement device according to claim 1, wherein the thermocouple-use connection terminal is made of the same material as the thermocouple in the biosensor with which it is in contact, or is made of an a compensating lead wire corresponding to the material of the thermocouple.

3. The measurement device according to claim 1, wherein the thermocouple-use connection terminals are both made of the same material, which is different from the materials constituting the thermocouple.

4. The measurement device according to claim 1, wherein the surface of the thermocouple-use connection terminals has undergone metal plating.

5. The measurement device according to claim 1, wherein the thermocouple provided to the biosensor, and a second thermocouple form a biosensor/measurement device integrated thermocouple via the thermocouple-use connection terminals.

6. The measurement device according to claim 5, wherein the ends of the second thermocouple disposed in the measurement device are disposed as close as possible.

7. The measurement device according to claim 6, wherein the ends of the second thermocouple are a reference temperature junction of the thermocouple, which is integrated with the biosensor,
and comprise an environmental temperature sensor to acquire the reference temperature/environmental temperature disposed on or near the reference temperature junction of the integrated thermocouple.

8. The measurement device according to claim 7, wherein the environmental temperature sensor individually has a first temperature sensor for acquiring the reference temperature of the integrated thermocouple, and a second temperature sensor for acquiring the environmental temperature of the measurement device.

9. The measurement device according to claim 1, wherein the thermocouple, which is provided on the biosensor, is configured to measure integrally the temperature of the measuring junction.

10. The measurement device according to claim 9, wherein the thermocouple-use connection terminals are such that the ends of the thermocouple on the biosensor are disposed as close as possible.

11. The measurement device according to claim 10, further comprising a reference temperature junction temperature sensor that is disposed in contact with the ends of the reference temperature junction of the thermocouple disposed in the biosensor, or nearby these ends, and is for acquiring the reference temperature/environmental temperature of the thermocouple.

12. The measurement device according to claim 11, wherein the reference temperature junction temperature sensor individually has a third temperature sensor for acquiring the reference temperature of the thermocouple disposed in the biosensor, and a fourth temperature sensor for acquiring the environmental temperature of the measurement device.

13. The measurement device according to claim 8, wherein the biosensor comprises:
the cavity for holding an analysis object;
the electrode system for measuring the analysis object; and
the thermocouple formed by joining the at least two dissimilar substances.

14. The measurement device according to claim 1, further comprising an arithmetic processing unit for calculating temperature information at the measuring junction, which is one of the junctions of the thermocouple formed in the biosensor, using as a reference the reference temperature/environmental temperature or the reference temperature.

15. The measurement device according to claim 14, wherein the arithmetic processing unit corrects the measured value that is the result of measuring the specific component in the drop of analysis object placed in the cavity, on the basis of the reference temperature/environmental temperature or the reference temperature.

16. The measurement device according to claim 14, wherein the arithmetic processing unit corrects the measured value that is the result of measuring the specific component in the drop of analysis object placed in the cavity, on the basis of the temperature information at the measuring junction.

17. The measurement device according to claim 15, wherein the arithmetic processing unit corrects the various correction items with respect to the result of measuring in the drop of analysis object placed in the cavity, on the basis of the reference temperature/environmental temperature or the reference temperature, and/or the temperature information at the measuring junction, and corrects the measured value on the basis of these temperature-corrected correction items.

18. The measurement device according to claim 14, further comprising a current/voltage conversion circuit for converting the current values measured by the electrode system and the environmental temperature sensor or the reference temperature junction sensor into voltage;
an amplifier circuit for amplifying the thermoelectromotive force;
an A/D converter circuit for converting the voltage converted by the current/voltage conversion circuit or the amplifier circuit into a digital signal; and
a memory device for recording the various measured values and the various temperature information converted into a digital signal by the A/D converter circuit,
wherein the arithmetic processing unit computes the various measured values and the various temperature information from the digital signals, and corrects the various measured values using the various temperature information according to various conditions.

19. The measurement device according to claim 18, wherein the memory device has a correction table used by the arithmetic processing unit for correcting the various correction items or the measured values corresponding to the environmental temperature or the reference temperature and the measuring junction temperature.

* * * * *

UNITED STATES PATENT AND TRADEMARK OFFICE
CERTIFICATE OF CORRECTION

PATENT NO.        : 8,845,966 B2  
APPLICATION NO.   : 13/707971  
DATED             : September 30, 2014  
INVENTOR(S)       : Takaaki Fujii Page 1 of 1

It is certified that error appears in the above-identified patent and that said Letters Patent is hereby corrected as shown below:

On the Title Page

In item (73), Assignee, "Panasonic Corporation, Osaka (JP)" should read --Panasonic Healthcare Co., Ltd., Ehime (JP)--

Signed and Sealed this  
Fourteenth Day of April, 2015

Michelle K. Lee  
*Director of the United States Patent and Trademark Office*